(12) United States Patent
Gotwals et al.

(10) Patent No.: US 6,652,856 B2
(45) Date of Patent: Nov. 25, 2003

(54) METHOD FOR THE TREATMENT OF FIBROSIS

(75) Inventors: Philip J. Gotwals, Needham, MA (US); Victor Kotelianski, Boston, MA (US)

(73) Assignee: Biogen, Inc., Cambridge, MA (US)

( * ) Notice: Subject to any disclaimer, the term of this patent is extended or adjusted under 35 U.S.C. 154(b) by 0 days.

(21) Appl. No.: 10/061,658

(22) Filed: Feb. 1, 2002

(65) Prior Publication Data

US 2002/0182213 A1 Dec. 5, 2002

Related U.S. Application Data

(63) Continuation of application No. 09/557,092, filed on Apr. 21, 2000, now abandoned.
(60) Provisional application No. 60/130,847, filed on Apr. 22, 1999, now abandoned, and provisional application No. 60/137,214, filed on Jun. 1, 1999, now abandoned.

(51) Int. Cl.[7] .............................................. A61K 39/395

(52) U.S. Cl. ............................ 424/133.1; 424/144.1; 424/173.1; 424/143.1

(58) Field of Search ...................... 424/130.1, 133.1, 424/139.1, 141.1, 152.1, 143.1; 530/387.1, 387.3, 387.9, 388.1, 388.2, 388.22

(56) References Cited

U.S. PATENT DOCUMENTS

| 4,683,195 A | 7/1987 | Mullis et al. |
| 5,789,650 A | 8/1998 | Lonberg et al. |
| 5,798,230 A | 8/1998 | Bornkamm et al. |

FOREIGN PATENT DOCUMENTS

| EP | 0239400 B1 | 9/1997 |
| WO | WO 90/07861 | 7/1990 |
| WO | WO9313798 | 7/1993 |
| WO | WO94 17828 | 9/1994 |
| WO | WO95 19790 | 7/1995 |
| WO | WO97 11718 | 4/1997 |
| WO | WO97 18838 | 5/1997 |

OTHER PUBLICATIONS shock et al., In Adhesion Molecules and the lung. Eds P. Ward and J. Fantone, Marcel Dekker, Inc., New Yrk, Chapter 8, pp. 177–209, 1996.*
Humphries MJ. Integrin cell adhesion receptors and the concept of agonism. Trends Pharmacol Sci. 21(1):29–32, 2000.*
Baldwin et al., 1998, Structure, 6:923–935, "Cation binding to the integrin CD11b I domain and activation model assessment".
Bennett et al., 1983, Proc. Natl. Acad. Sci., 80:2417–2421, "Inhibition of fibrinogen binding to stimulated human platelets by a monoclonal antibody".
Boerner et al., 1991, J. Immunol., 147:86–95, "Production of Antigen–Specific Human Monoclonal Antibodies From In Vitro–Primed Human Splenocytes".
Border et al., 1994, New England J. Medicine, 331:1286–1292, "Transforming Growth Factor Beta In Tissue Fibrosis".
Bossy et al., 1991, EMBO J., 10:2375–2385, "Characterization of the integrin Alpha8 subnit: A new intefrin beta1–associated subunit, which is prominently expressed on axons and on cells in contact with basal laminae in chick embryos".
Briesewitz et al., 1993, J. of Biol. Chemistry, 268:2989–2996, "Expression of Native and Truncated Forms of the human integrin Alpha1 1 subunit*".
Bridges et al., 1995, Mol. Immunol., 32:1329–2989, "Variable Region cDNA Sequences and Characterization of Murine Anti–Human Interferon y Receptor Monoclonal Antibodies that Inhibit Receptor Binding By Interferon y".
Camper et al., 1998, J. Biol. Chem., 273:20383–20389, "Isolation, Cloning, and Sequence Analysis of the Integrin Subunit a10, a Beta1–associated Collagen Binding Integrin Expressed on Chondrocytes*".
Cerf–Bensussan et al., 1992, Eur. J. Immunol. 22:273–277, "The human intraepithelial lymphocyte marker HML–1 is an integrin consisting of a Beta7 subunit associated with a distinctive alpha chain".
Clackson et al., 1991, Nature, 352:624–628, "Making antibody fragments using phage display libraries".
Co et al., 1991, Proc. Natl Acad. Sci., 88:2869–2873, "Humanized anotbodies for antiviral therapy".
Colbert et al, 1991, J. of Immunol. Methods, 140: 227–233, "The effect of fluorescein labels on the affinity of antisera to small haptens".
Corbi and Miller et al., 1987, J. of Biol. Chem. 263: 12403–12411, "cDNA cloning and complete primary struction fo the alpha subunit of a leukocyte adhesion glycoprotein, p150,95".
Corbi and Kishimoto et al., 1988, J. of Biol. Chem., 263: 12403–12411, "The Human Leukocyte Adhesion Glycoprotein Mac–1 (Complement Receptor Type 3, CD11b) alpha Subunit".
Davies, 1989, J. of Cell Biology, 109: 1817–1826, "The Osteoclast Functional Antigen, Implicated in the Regulation of Bone Resorption, Is Biochemically Related to the Vitronectin Receptor".
Diamond et al., 1993, 120: 1031–1043, "The I Domain Is a Major Recognition Site on the Luekocyte Intgegrin Mac–1 (CD–11b/CD18) For Four Distinct Adhesion Ligands".

(List continued on next page.)

*Primary Examiner*—Christina Chan
*Assistant Examiner*—Maher Haddad

(57) ABSTRACT

Disclosed is a method of treating fibrosis in a human or animal subject. The method comprises administering to the subject an effective amount of an antibody to an integrin or fragment thereof.

8 Claims, 10 Drawing Sheets

OTHER PUBLICATIONS

Edwards et al., 1995, 270:12635–12640, "Identification of Amino Acids in the CD11a I–domain Important for Binding of the Leukocyte Function–associated Antigen–1 (LFA–1) to Intercellular Adhesion Molecules–1 (ICAM–1)*".

Gotwals et al., 1996, J. Clin. Invest., 97:2469–2477, "The alpha1beta1 Integrin is expressed during Neointima Formation in Rat Arteries and Mediates Collagen Matrix Reorganization".

Grayson et al., 1998, J. Exp. Med. 188:2187–2191, "alphabeta2 Integrin Is Expressed on Human Eosinophils and Functions as an Alternative Ligand for Vascular Cell Adhesion Molecule 1 (VCAM–1)".

Hemler et al., 1984, J. of Imunnol., 132:3011–3018, "Glycoproteins of 210,000 and 130,000 M.W. On Activated T Cells: Cell Distribution And Antigenic Relation To Components On Resting Cells And T Cell Lines".

Hemler et al., 1987, J. of Immunol., 262:11478–11485, "Characterization of the Cell Surface Heterodimer VLA–4 and Related Peptides".

Hessle et al., 1984, Differentiation, 26:49–54, "Basement membrane diversity detected by monoclonal antibodies".

Ignatius et al., 1990, J. of Cell Biology, 111:709–720, "Molecular Cloning of the Rat Integrin alpha1 Subunit: A Receptor for Laminin and Collagen".

Kamata et al., 1995, J. of Biological Chem. 270:12531–12535, "Critical Threonine and Aspartic Acid Residues within the I Domains of beta2 Integrins for Interactions with Intercellular Adhesion Molecule 1 (ICAM–1) and C3bi*".

Keely et al., 1995, J. of Cell Science, 108:595–607, "Alteration of collagen–dependent adhesion, motility, and morphogenesis by the expression of antisense alpha2 integrin mRNA in mammary cells".

Kern et al., 1994, J. of Biol. Chem., 269:22811–55816, "The Role of the I Domain in Ligand Binding of the Human Integrin alpha1beta1".

Langholz et al., 1995, J. of Cell Biol., 131:1903–1915, "Collagen and Collagenase Gene Expression in Three–dimensional Collagen Lattices Are Differentially Regulated by alpha1beta1 and alpha2beta1 Integrins".

Larson et al., 1989, J. of Cell Biol., 108:703–712, "Primary Structure of the Leukocyte Function–associated Molecule–1 alpha Subunit: an Integrin with an Embedded Domain Defining a Protein Superfamily".

Lee et al., 1995, Structure, 3:1333–1340, "Two conformations of the integrin A–domain (I–domain): a pathway for activation?"

Lowry et al., 1951, Dept. of Pharma., Washington Univ. School of Med., 265–275, "Protein Measurement with the folin phenol reagent*".

Mendrick et al., 1995, Labratory Investigation, 72:367–375, "Glomerular Epithelial and Mesangial Cells Differentially Modulate the Binding Specificities of VLA–1 and VLA–2".

Michisita et al., 1993, Cell Press, 72:857–867, "A Novel Divalent Cation–Binding Site in the A Domain of the Beta2 Integrin CR3 (CD11b/CD18) Is Essential for Ligand Binding".

Nagler et al., 1996, Am. J. Respir.Crit. Care Med., 154:1082–1086, "Reduction in Pulmonary Fibrosis In Vivo by Halofuginone".

Nishimura et al., 1994, J. of Biol. Chem., 269:28708–28715, "Integrin–αvBeta8".

Orlandi, 1989, Proc. Natl. Acad. Sci., 86:3833–3837, "Cloning immunoglobulin variable domains for expression by the polymerase chain reaction".

Persson et al., 1991, Proc. Natll. Acad. Sci., 88:2432–2436, "Generation of diverse high–affinity human monoclonal antibodeis by repertoire cloning".

Pischel et al., 1987, J. of Immunol., 138:226–233, "Use of the monoclonal antibody 12F1 to Characterize the Differentiation Antigen VLA–21".

Qu et al., 1995, Proc. Natl. Acad. Sci., 92:10277–10281, "Crystal structure of the I–domain form the CD11a/CD18 (LFA–1, aLbeta2) integrin".

Qu et al., 1996, Structure, 4:931–942, "The role of the divalent cation in the structure of the I domain from the CD11a/CD18 integrin".

Queen et al., 1989, Proc. Natl. Acad. Sci., 86:10029–10033, "A humanized antibody that binds to the interleukin 2 receptor".

Riechmann et al., 1988, Nature, 332:323–327, "Reshaping human antibodies for therapy".

Riikonen et al., 1994, J. of Biol. Chem., 270:376–382, "Transforming Growth Factor–beta Regulates Collagen Gel . . .".

Sanchez–Madrid et al., 1982, Immunol., 79:7489–7493, "Three distinct antigens associated with human T–lymphocyte–mediated cytolysis: . . .".

Schiro et al., 1991, Cell, 67:403–410, "Integrin alpha2beta1 (lvla–2) Mediates Reorginazation and Contraction of Collagen Matrices by Human Cells".

Shaw et al., 1994, J. of Biol. Chem., 269:6016–6025, "Molecular Cloning of the Human Mucosal Lymphocyte Integrin alphaE Subunit".

Sonnenberg et al., 1987, J. of Biol. Chem., 262:10376–10383, "A Complex of Platelet Glycoproteins Ic and IIa Identified by a Rat Monoclonal Antibody*".

Springer et al., 1990, Nature, 346:425–434, "Adhesion receptors of the immune system".

Stacker et al., 1991, J. of Immunol., 146:648–655, "Leukocyte Integrin P150,95 (CD11c/CD18) Functions . . .".

Takada et al., 1989, J. of Cell Biol., 109:397–407, "The Primary Structure of the VLA–2/Collagen Receptor alpha2 Subunit . . .".

Tempest et al., 1991, Bio/Tech., 9:266–271, "Reshaping A Human Monoclonal Antibody To Inhibit Human Respiratory Syncytical Virus Infection In Vivo".

Van der Vieren et al., 1995, Immunity, 3:683–690, "A Novel Leukointegrin, alphadbeta2, Binds Preferentially to ICAM–3".

Verhoeyen et al., 1987, Science, 239:1534–1536, "Reshaping Human Antibodies: Grafting an Antilysozyme Activity".

Wang et al., 1996, Am. J. Respir. Cell Mol. Biol., 15:664–672, "Differential Regulation of Airway Epithelian Integrins . . .".

Ward et al., 1989, Nature, 341:544–546, "Binding activities of a repertoire of single immunoglobulin variable domains . . .".

Wayner et al., 1988, "J. of Cell Biol., 107:1881–1891, The Function of Multiple Extracellular Matrix Receptors . . .".

Weinacker et al., 1993, J. of Biol. Chem., 269:6940–6948, "Role of the Integrin alphavbeta6 in Cell Attachement to Fibronectin".

Woessner et al., 1961, Arch. of Biochem. and Biophys., 93:440–447, "The Determination of Hydroxyproline in Tissue . . .".

Yao et al., 1996, J. of Cell Science, 109:3139–3150, "Laminins promote the locomotion of skeletal myobl sts . . . ".

Pappadopoulos, et al; Verh. Dtsch. Ges. Path. 77, 292–295 (1993) (German) abstract.

Hokibara, et al., Cln Exp Immunol. 1998: 114: 236–44 (United Kingdom).

Roy–Chaudhury, et al., Kidney International, vol. 49 (1996); pp. 127–134 (US).

Lin, et al., Current Opinion in chemical Biology, vol. 2, No. 4, Aug. 1998 (1998–08), pp. 453–457 (United Kingdom).

Robb, et al., Journal of Clinical Investigation, vol. 94, No. 5, Nov. 1994 (1994–11), pp. 1722–1728 (U.S.).

Robb, et al. European Respiratory Journal, Supplement, vol. 9, No. supp. 22, Aug. 1996 (1996–08) (Denmark).

* cited by examiner

```
  1    V  S  P  T  F  Q  V  V  N  S  F  A  P  V  Q  E  C  S  T  Q
                                    I
 21    L  D  I  V  I  V  L  D  G  S  N  S  I  Y  P  W  E  S  V  I
                                                      D           T
 41    A  P  L  N  D  L  L  K  R  M  D  I  G  P  K  Q  T  Q  V  G

61    I  V  Q  Y  G  E  N  V  T  H  E  F  N  L  N  K  Y  S  S  T

81    E  E  V  L  V  A  A  K  K  I |G  R  Q  G  G  L| Q  T  M  T
                                    |V  Q  R  G  G  R|
101    A  L  G  I  D  T  A  R  K  E  A  F  T  E  A  R  G  A  R  R
             T
121    G  V  K  K  V  M  V  I  V  T  D  G  E  S  H  D  N  Y  R  L
                                                            H
141    K  Q  V  I  Q  D  C  E  D  E  N  I  Q  R  F  S  I  A  I  L
          K
161    G  H  Y  N  R  G  N  L  S  T  E  K  F  V  E  E  I  K  S  I
          S
181    A  S  E  P  T  E  K  H  F  F  N  V  S  D  E  L  A  L  V  T

201    I  V  K  A  L  G  E  R  I  F  A  L  E  A
                T
```

| | |
|---|---|
| 1 | V S P T F Q V V N S I A P V Q E C S T Q |
| 21 | L D I V I V L D G S N S I Y P W D S V T |
| 41 | A F L N D L L K R M D I G P K Q T Q V G |
| 61 | I V Q Y G E N V T H E F N L N K Y S S T |
| 81 | E E V L V A A K K I <u>V Q R G G R</u> Q T M T |
| 101 | A L G T D T A R K E A F T E A R G A R R |
| 121 | G V K K V M V I V T D G E S H D N H R L |
| 141 | K K V I Q D C E D E N I Q R F S I A I L |
| 161 | G S Y N R G N L S T E K F V E E I K S I |
| 181 | A S E P T E K H F F N V S D E L A L V T |
| 201 | I V K T L G E R I F A L E A |

FIG. 5

METHOD FOR THE TREATMENT OF FIBROSIS

RELATED APPLICATIONS

This application is a continuation of U.S. patent application Ser. No. 09/557,092, filed Apr. 21, 2000, now abandoned, which was a continuation in part of U.S. patent application Ser. No. 60/130,847, filed Apr. 22, 1999, now abandoned, and U.S. patent application Ser. No. 60/137,214, filed Jun. 1, 1999, now abandoned. The instant application claims priority from each of these earlier-filed applications.

FIELD OF THE INVENTION

This invention relates to methods for treating fibrosis in subjects in need of such treatment.

BACKGROUND OF THE INVENTION

Collagen is a fibril-forming protein which is essential for maintaining the integrity of the extracellular matrix found in connective tissues. The production of collagen is a highly regulated process, and its disturbance may lead to the development of tissue fibrosis. While the formation of fibrous tissue is part of the normal beneficial process of healing after injury, in some circumstances there is an abnormal accumulation of fibrous materials such that it may ultimately lead to organ failure (Border et al. (1994) *New Engl. J. Med.* 331:1286–1292). Injury to any organ leads to a stereotypical physiological response: platelet-induced hemostasis, followed by an influx of inflammatory cells and activated fibroblasts. Cytokines derived from these cell types drive the formation of new extracellular matrix and blood vessels (granulation tissue). The generation of granulation tissue is a carefully orchestrated program in which the expression of protease inhibitors and extracellular matrix proteins is upregulated, and the expression of proteases is reduced, leading to the accumulation of extracellular matrix.

Central to the development of fibrotic conditions, whether induced or spontaneous, is stimulation of fibroblast activity. The influx of inflammatory cells and activated fibroblasts into the injured organ depends on the ability of these cell types to interact with the interstitial matrix, which contains primarily collagens. The major cell surface collagen receptors are the $\alpha1\beta1$ (VLA-1) and $\alpha2\beta1$ (VLA-2) integrins. Both integrins have been implicated in cell adhesion and migration on collagen (Keely et al. (1995) *J. Cell Sci.* 108:595–607 and Gotwals et al. (1996) *J. Clin. Invest.* 97: 2469–2477); in promoting contraction of collagen matrices (Gotwals et al. (1996) *J. Clin. Invest.* 97: 2469–2477 and Schiro, (1991) *Cell* 67:403–410), and in regulating the expression of genes involved in the remodeling of the extracellular matrix (Riikonen et al. (1995) *J. Biol. Chem.* 270:1–5 and Langholz et al. (1995) *J. Cell Biol.* 131: 1903–1915). For example, when fibroblasts contact a collagen matrix, signaling through the $\alpha1\beta1$ integrin down-regulates collagen I expression, while signaling through $\alpha2\beta1$ up-regulates the expression of matrix metalloproteases (Langholz et al. (1995) *J. Cell Biol.* 131: 1903–1915).

Many of the diseases associated with the proliferation of fibrous tissue are both chronic and often debilitating, including for example, skin diseases such as scleroderma. Some, including pulmonary fibrosis, can be fatal due in part to the fact that the currently available treatments for this disease have significant side effects and are generally not efficacious in slowing or halting the progression of fibrosis (Nagler et al. 1996, *Am. J. Respir. Crit. Care Med.*, 154:1082–86).

There is, accordingly, a continuing need for new anti-fibrotic agents.

In contrast to the trends in research in the field of anti-fibrotic therapy which has focused on upstream cytokine mediators of fibrosis, such as TGF-$\beta$, we propose the use of antibody molecules comprising antigen binding regions derived from the heavy or light chain variable regions of an anti-VLA antibody, for use in anti-fibrotic treatment and specifically for treatment of pulmonary fibrosis.

SUMMARY OF THE INVENTION

The present invention provides a method of treating fibrosis in a subject. Specifically, the invention provides a method for treating fibrosis by administering to a patient a pharmaceutical composition containing an effective amount of an antibody molecule having antigen binding regions derived from the light and heavy chain variable regions of an anti-VLA antibody. In a preferred embodiment, the anti-VLA antibody is anti-VLA-1, -2, -3, -4, -5, and -6. In a most preferred embodiment, the invention provides a method for treating pulmonary fibrosis by administering to a patient a pharmaceutical composition containing an effective amount of an antibody molecule having antigen binding regions derived from the light and heavy chain variable regions of an anti-VLA-1 and anti-VLA-2 antibody.

The anti-VLA antibody can be selected from the group consisting of a human antibody, a chimeric antibody, a humanized antibody and fragments thereof. The anti-VLA antibody can be a monoclonal or polyclonal antibody.

The invention further provides a method for treating fibrosis in a subject that is a human or animal subject.

All of the cited literature in the preceding section, as well as the cited literature included in the following disclosure, are hereby incorporated by reference.

DESCRIPTION OF THE DRAWINGS

FIG. 1A. Increasing concentrations of the human $\alpha1$-I domain were bound to plates previously coated with 1 $\mu$g/ml collagen I (squares) or collagen IV (circles). Values shown have been corrected for background binding to BSA. FIG. 1B. 2 $\mu$g/ml human $\alpha1$-I domain was mixed with increasing concentration of an anti-human $\alpha1\beta1$ integrin antibody 5E8D9 (squares) or an anti-human $\alpha2\beta1$-integrin antibody A2IIE10 (circles), and then bound to plates previously coated with 1 $\mu$g/ml collagen IV. FIG. 1C. Plates were coated with 1 $\mu$g/ml collagen IV or 3% BSA. $\alpha1$-I domain (2 $\mu$g/ml) was subsequenctly bound to coated plates plates in the presence of 1 mM $Mn^{2+}$, 1 mM $Mg^{2+}$, or 5 mM EDTA. Data shown is representative of three independent experiments.

FIG. 2A. Increasing concentration of mAbs AEF3 (triangles) or AJH10 (ATCC NO. PTA-3580) (circles) were bound to plates coated with 30 $\mu$g/ml $\alpha1$-I domain. FIG. 2B. The $\alpha1$-I domain was treated with increasing concentrations of mAb AJH10 (ATCC NO. PTA-3580) (diamonds) or mAb BGC5 (squares) and bound collagen IV (2 $\mu$g/ml) coated plates. FIG. 2C. K562-$\alpha1$ cell were treated with increasing concentration of mAbs AEF3(triangles) or AJH10 (ATCC NO. PTA-3580) (circles) and bound to collagen IV (5 $\mu$g/ml) coated plates. 45–50% of cells added to each well adhered to collagen IV. Data shown is representative of three independent experiments. The hybridoma that produces the $\alpha1$ domain antibody AJH10 was deposited under the Budapest Treaty on Aug. 2, 2001 with the American Type Culture Collection, 10801 University Boulevard, Manassas, Va. 20110-2209 (ATCC PTA-3580). Other materials necessary to make AJH10 are available in the public domain to those of ordinary skill in the art.

FIG. 3B. Rabbit vascular smooth muscle cells were incubated with either mAb AJH10 (ATCC NO. PTA-3580) (bottom) or murine IgG control (top) and analyzed by fluorescence activated cell sorter (FACS).

FIG. 4A Amino acid sequence of the rat (top) (SEQ ID NO: 5) and human (below) (SEQ ID NO: 6) α1-I integrin polypeptide sequences. The residues that comprise the MIDAS (metal ion dependent site adhesion site) motif are shown in bold. The human amino acids (SEQ ID NO: 8) that replaced the corresponding rat residues (SEQ ID NO: 7) in RΔH are shown in the boxed region. For clarity, residue numbering in the text refers to this FIG. 4B. Increasing concentrations of mAb AJH10 (ATCC No. PTA-3580) were bound to plates coated with 30 μg/ml human (circles), rat (triangles) or RΔH (squares) α1-I domain. Data shown is representative of three experiments.

FIG. 5. FIG. 5 illustrates the amino acid sequence of the human α1-I integrin polypeptide sequence (SEQ ID NO: 9). The amino acid sequence of the epitope for the anti-α1-I domain blocking mAbs (SEQ ID NO: 8) is shown in the box.

FIG. 6A. 0.5 μg of blocking mAb AJH10 (ATCC No. PTA-3580) or non-blocking mAb AEF3 in the presence of 5 mM EDTA (open) or 1 mM $MnCl_2$ (solid) were bound to plates previously coated with 1 μg/ml affinity purified, human α1β1 integrin. FIG. 6B. 5 μg/ml AJH10 (ATCC No. PTA-3580) or AEF3 were incubated with K562-α1 cells in the presence of 2 mM $MnCl_2$ (solid), or following a wash with 5 mM EDTA (open). Bound antibody was measured by FACS and is reported as the mean fluorescence intensity (MFI).

DETAILED DESCRIPTION OF THE INVENTION

Figure 1A:
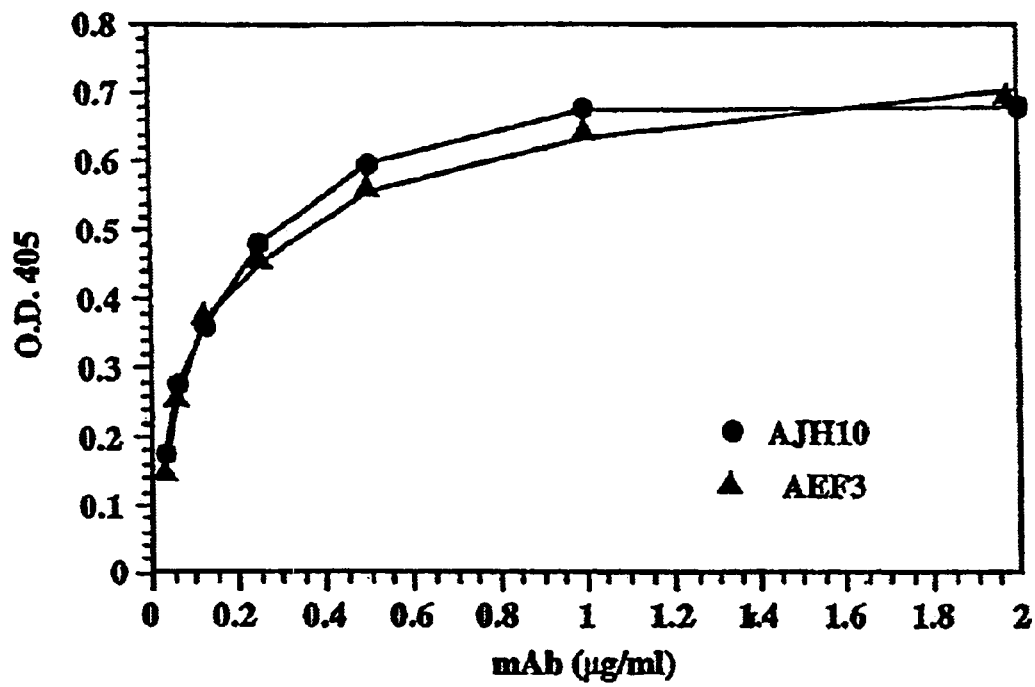
FIG. 1A–FIG. 1C. The $\alpha1$-I domain binds collagen.

The present application is directed to the discovery that antibodies to integrins and fragments thereof can be used for the treatment of fibrosis.

The methods of the present invention contemplate the use of antibodies to integrins where the integrins contemplated include molecules which comprise a β chain, including but not limited to β1, β2, β3, β4, β5, β6, β7, β8, non-covalently bound to an α chain, including but not limited to α1, α2, α3, α4, α5, α6, α7, α8, α9, α10, αV, αL, αM, αX, αD, αE, αIIb. Examples of the various integrins contemplated for use in the invention include, but are not limited to:

α1β1, α2β1, α3β1, α4β1, α5β1, α6β1, α7β1, α8β1, α9β1, α10β1, αVβ1, αLβ1, αMβ1, αXβ1, αDβ1, αIIbβ1, αEβ1;

α1β2, α2β2, α3β2, α4β2, α5β2, α6β2, α7β2, α8β2, α9β2, α10β2, αVβ2, αLβ2, αMβ2, αXβ2, αDβ2, αIIbβ2, αEβ2;

α1β3, α2β3, α3β3, α4β3, α5β3, α6β3, α7β3, α8β3, α9β3, α10β3, αVβ3, αLβ3, αMβ3, αXβ3, αDβ3, αIIbβ3, αEβ3;

α1β4, α2β4, α3β4, α4β4, α5β4, α6β4, α7β4, α8β4, α9β4, α10β4, αVβ4, αLβ4, αMβ4, αXβ4, αDβ4, αIIbβ4, αEβ4;

α1β5, α2β5, α3β5, α4β5, α5β5, α6β5, α7β5, α8β5, α9β5, α10β5, αVβ5, αLβ5, αMβ5, αXβ5, αDβ5, αIIbβ5, αEβ5;

α1β6, α2β6, α3β6, α4β6, α5β6, α6β6, α7β6, α8β6, α9β6, α10β6, αVβ6, αLβ6, αMβ6, αXβ6, αDβ6, αIIbβ6, αEβ6;

α1β7, α2β7, α3β7, α4β7, α5β7, α6β7, α7β7, α8β7, α9β7, α10β7, αVβ7, αLβ7, αMβ7, αXβ7, αDβ7, αIIbβ7, αEβ7;

α1β8, α2β8, α3β8, α4β8, α5β8, α6β8, α7β8, α8β8, α9β8, α10β8, αVβ8, αLβ8, αMβ8, αXβ8, αDβ8, αIIbβ8, αEβ8;

The methods of the present invention also contemplate the use of antibodies to integrin fragments including for example antibodies to a β chain alone, including but not limited to β1, β2, β3, β4, β5, β6, β7, β8, as well as an α chain alone, including but not limited to α1, α2, α3, α4, α5, α6, α7, α8, α9, α10, αV, αL, αM, αX, αD, αE, αIIb. In addition, the methods of the present invention further contemplate the use of antibodies to integrin fragments including for example antibodies to the I domain of the α chain, including but not limited to the I domain from α1β1 (Briesewitz et al., 1993 J. Biol. Chem. 268:2989); α2β1 (Takada and Hemler, 1989 J Cell Biol 109:397), αLβ2 (Larson et al., 1989 J Cell Biol 108:703), αMβ2 (Corbi et al., 1988 J Biol Chem 263:12403), αXβ2 (Corbi et al., 1987 EMBO J 6:4023), αDβ2 (Grayson et al., 1988 J Exp Med 188:2187), αEβ7 (Shaw et al., 1994 J Biol Chem 269:6016). In a preferred embodiment, the alpha1-I domain antigenic determinant comprises an amino acid sequence of at least 6 contiguous amino acids, wherein the contiguous sequence is found within the sequence of FIG. 5 (SEQ ID NO:9). Moreover, in a preferred embodiment, the contiguous sequence is Val-Gln-Arg-Gly-Gly-Arg (SEQ ID NO:10).

In a preferred embodiment the invention contemplates the use of antibodies to VLA-1, -2, -3, -4, -5, -6, in which each of the molecules comprise a β1 chain non covalently bound to a α chain, (α1, α2, α3, α4, α5, α6), respectively. In a most preferred embodiment, the invention contemplates using anti-VLA-1 and anti-VLA-2 antibodies for the treatment of pulmonary fibrosis.

Methods for producing integrins for use in the present invention are known to those of skill in the art (see for e.g. Springer et al. 1990, *Nature* 346:425–434).

Embodiments of the present invention include polyclonal and monoclonal antibodies to integrins and fragments thereof. Preferred embodiments of the present invention include a monoclonal antibody, including for example, an anti-VLA antibody homolog. Preferred antibodies and homologs for treatment, in particular for human treatment, include human antibody homologs, humanized antibody homologs, chimeric antibody homologs, Fab, Fab', F(ab')2 and F(v) antibody fragments, and monomers or dimers of antibody heavy or light chains or mixtures thereof. Thus, monoclonal antibodies against an integrin molecule or fragment thereof are the preferred binding agent in the method of the invention.

As used herein, the term "antibody homolog" includes intact antibodies consisting of immunoglobulin light and heavy chains linked via disulfide bonds. The term "antibody homolog" is also intended to encompass a protein comprising one or more polypeptides selected from immunoglobulin light chains, immunoglobulin heavy chains and antigen-binding fragments thereof which are capable of binding to one or more antigens (i.e., VLA-1, VLA-2, VLA-3, VLA-4, VLA-5, VLA-6). The component polypeptides of an antibody homolog composed of more than one polypeptide may optionally be disulfide-bound or otherwise covalently crosslinked.

Accordingly, therefore, "antibody homologs" include intact immunoglobulins of types IgA, IgG, IgE, IgD, IgM (as well as subtypes thereof), wherein the light chains of the immunoglobulin may be of types kappa or lambda.

"Antibody homologs" also include portions of intact antibodies that retain antigen-binding specificity, for example, Fab fragments, Fab' fragments, F(ab')2 fragments, F(v) fragments, heavy chain monomers or dimers, light chain monomers or dimers, dimers consisting of one heavy and one light chain, and the like. Thus, antigen-binding fragments, as well as full-length dimeric or trimeric polypeptides derived from the above-described antibodies are themselves useful.

As used herein, a "humanized antibody homolog" is an antibody homolog, produced by recombinant DNA technology, in which some or all of the amino acids of a human immunoglobulin light or heavy chain that are not required for antigen binding have been substituted for the corresponding amino acids from a nonhuman mammalian immunoglobulin light or heavy chain.

As used herein, a "chimeric antibody homolog" is an antibody homolog, produced by recombinant DNA technology, in which all or part of the hinge and constant regions of an immunoglobulin light chain, heavy chain, or both, have been substituted for the corresponding regions from another immunoglobulin light chain or heavy chain. In another aspect the invention features a variant of a chimeric molecule which includes: (1) a VLA targeting moiety; (2) optionally, a second peptide, e.g., one which increases solubility or in vivo life time of the VLA targeting moiety, e.g., a member of the immunoglobulin super family or fragment or portion thereof, e.g., a portion or a fragment of IgG, e.g., the human IgGl heavy chain constant region, e.g., CH2 and CH3 hinge regions; and a toxin moiety. The chimeric molecule can be used to treat a subject, e.g., a human, at risk for disorder related to proliferation of epithelial cells such as hair follicles and the like.

As used herein, a "human antibody homolog" is an antibody homolog produced by recombinant DNA technology, in which all of the amino acids of an immunoglobulin light or heavy chain that are derived from a human source.

A "a subject with a fibrotic condition" refers to, but is not limited to, subjects afflicted with fibrosis of an internal organ, subjects afflicted with a dermal fibrosing disorder, and subjects afflicted with fibrotic conditions of the eye.

Fibrosis of internal organs (e.g., liver, lung, kidney, heart blood vessels, gastrointestinal tract), occurs in disorders such as pulmonary fibrosis, myelofibrosis, liver cirrhosis, mesangial proliferative glomerulonephritis, crescentic glomerulonephritis, diabetic nephropathy, renal interstitial fibrosis, renal fibrosis in patients receiving cyclosporin, and HIV associated nephropathy. In a preferred embodiment, the invention contemplates using the anti-VLA antibodies for the treatment of pulmonary fibrosis. In a most preferred embodiment, the invention contemplates using anti-VLA-1 and anti-VLA-2 antibodies for the treatment of pulmonary fibrosis.

Dermal fibrosing disorders include, but are not limited to, scleroderma, morphea, keloids, hypertrophic scars, familial cutaneous collagenoma, and connective tissue nevi of the collagen type.

Fibrotic conditions of the eye include conditions such as diabetic retinopathy, postsurgical scarring (for example, after glaucoma filtering surgery and after cross-eye surgery), and proliferative vitreoretinopathy.

Additional fibrotic conditions which may be treated by the methods of the present invention include: rheumatoid arthritis, diseases associated with prolonged joint pain and deteriorated joints; progressive systemic sclerosis, polymyositis, dermatomyositis, eosinophilic fascitis, morphea, Raynaud's syndrome, and nasal polyposis.

In addition, fibrotic conditions which may be treated the methods of present invention also include inhibiting overproduction of scarring in patients who are known to form keloids or hypertrophic scars, inhibiting or preventing scarring or overproduction of scarring during healing of various types of wounds including surgical incisions, surgical abdominal wounds and traumatic lacerations, preventing or inhibiting scarring and reclosing of arteries following coronary angioplasty, preventing or inhibiting excess scar or fibrous tissue formation associated with cardiac fibrosis after infarction and in hypersensitive vasculopathy.

An "effective amount" (when used in the toleragenic context) is an amount sufficient to effect beneficial or desired clinical results. An effective amount can be administered in one or more administrations. In terms of treatment, an "effective amount" of an antibody for use in the present invention, including for example an anti-VLA antibody, is an amount sufficient to palliate, ameliorate, stabilize, reverse, slow or delay progression of a fibrotic condition in accordance with clinically acceptable standards for disorders to be treated or for cosmetic purposes. Detection and measurement of indicators of efficacy may be measured by a number of available diagnostic tools, including, for example, by physical examination including blood tests, pulmonary function tests, and chest X-rays; CT scan; bronchoscopy; bronchoalveolar lavage; lung biopsy and CT scan.

Methods of Making Antibodies

The technology for producing monoclonal antibodies, including for example, anti-integrin monoclonal antibodies is well known. See for example, Mendrick et al. 1995, *Lab. Invest.* 72:367–375 (mAbs to murine anti-$\alpha1\beta1$, and anti-$\alpha2\beta1$); Sonnenberg et al. 1987 *J. Biol. Chem.* 262:10376–10383 (mAbs to murine anti-$\alpha6\beta1$); Yao et al. 1996, *J Cell Sci* 1996 109:3139–50 (mAbs to murine anti-$\alpha7\beta1$); Hemler et al. 1984, *J Immunol* 132:3011–8 (mAbs to human $\alpha1\beta1$); Pischel et al. 1987 *J Immunol* 138:226–33 (mAbs to human $\alpha2\beta1$); Wayner et al. 1988, *J Cell Biol* 107:1881–91 (mAbs to human $\alpha3\beta1$); Hemler et al. 1987 *J*

*Biol Chem* 262:11478–85 (mAbs to human α4β1); Wayner et al. 1988 *J Cell Biol* 107:1881–91 (mAbs to human α5β1); Sonnenberg et al. 1987, *J. Biol. Chem.* 262:10376–10383 (mAbs to human α6β1); A Wang et al. 1996 *Am. J. Respir. Cell Mol. Biol.* 15:664–672 (mAbs to human α9β1); Davies et al. 1989 *J Cell Biol* 109:1817–26 (mAbs to human αV β1); Sanchez-Madrid et al. 1982, *Proc Natl Acad Sci U S A* 79:7489–93 (mAbs to human αL β2); Diamond et al. 1993, *J Cell Biol* 120:1031–43 (mAbs to human αMβ2); Stacker et al. 1991 *J Immunol* 146:648–55 (mAbs to human αXβ2); Van der Vieren et al 1995 *Immunity* 3:683–90 (mAbs to human αDβ2); Bennett et al. 1983 *Proc Natl Acad Sci U S A* 80:2417–21 (mAbs to human αIIbβ3); Hessle et al. 1984, *Differentiation* 26:49–54 (mAbs to human α6β4); Weinacker et al. 1994 *J Biol Chem* 269:6940–8 (mAbs to human αVβ5); Weinacker et al. 1994 *J Biol Chem* 269:6940–8 (mAbs to human αVβ6); Cerf-Bensussan et al 1992 *Eur J Immunol* 22:273–7 (mAbs to human αEβ7); Nishimura et al. 1994 *J Biol Chem* 269:28708–15 (mAbs to human αVβ8); Bossy et al. 1991 *EMBO J* 10:2375–85 (polyclonal antisera to human α8β1); Camper et al. 1998 *J. Biol. Chem.* 273:20383–20389 (polyclonal antisera to human α10β1).

In general, an immortal cell line (e.g., a myeloma cell line) is derived from the same mammalian species as the lymphocytes. Preferred immortal cell lines are mouse myeloma cell lines that are sensitive to culture medium containing hypoxanthine, aminopterin and thymidine ("HAT medium"). Typically, HAT-sensitive mouse myeloma cells are fused to mouse splenocytes using 1500 molecular weight polyethylene glycol ("PEG 1500"). Hybridoma cells resulting from the fusion are then selected using HAT medium, which kills unfused and unproductively fused myeloma cells (unfused splenocytes die after several days because they are not transformed). Hybridomas producing a desired antibody are detected by screening the hybridoma culture supernatants. For example, hybridomas prepared to produce anti-VLA antibodies may be screened by testing the hybridoma culture supernatant for secreted antibodies having the ability to bind to a recombinant VLA-expressing cell line.

To produce anti-VLA antibody homologs that are intact immunoglobulins, hybridoma cells that tested positive in such screening assays were cultured in a nutrient medium under conditions and for a time sufficient to allow the hybridoma cells to secrete the monoclonal antibodies into the culture medium. Tissue culture techniques and culture media suitable for hybridoma cells are well known. The conditioned hybridoma culture supernatant may be collected and the anti-VLA antibodies optionally further purified by well-known methods.

Alternatively, the desired antibody may be produced by injecting the hybridoma cells into the peritoneal cavity of an unimmunized mouse. The hybridoma cells proliferate in the peritoneal cavity, secreting the antibody which accumulates as ascites fluid. The antibody may be harvested by withdrawing the ascites fluid from the peritoneal cavity with a syringe.

Fully human monoclonal antibody homologs against VLA are another preferred binding agent which may block antigens in the method of the invention. In their intact form these may be prepared using in vitro-primed human splenocytes, as described by Boerner et al., 1991, J. Immunol. 147:86–95, "Production of Antigen-specific Human Monoclonal Antibodies from In Vitro-Primed Human Splenocytes".

Alternatively, they may be prepared by repertoire cloning as described by Persson et al., 1991, Proc. Nat. Acad. Sci. USA 88: 2432–2436, "Generation of diverse high-affinity human monoclonal antibodies by repertoire cloning" and Huang and Stollar, 1991, J. Immunol. Methods 141: 227–236, "Construction of representative immunoglobulin variable region CDNA libraries from human peripheral blood lymphocytes without in vitro stimulation" . U.S. Pat. No. 5,798,230 (Aug. 25, 1998, "Process for the preparation of human monoclonal antibodies and their use") describes preparation of human monoclonal antibodies from human B cells. According to this process, human antibody-producing B cells are immortalized by infection with an Epstein-Barr virus, or a derivative thereof, that expresses Epstein-Barr virus nuclear antigen 2 (EBNA2). EBNA2 function, which is required for immortalization, is subsequently shut off, which results in an increase in antibody production.

In yet another method for producing fully human antibodies, U.S. Pat. No. 5,789,650 (Aug. 4, 1998, "Transgenic non-human animals for producing heterologous antibodies") describes transgenic non-human animals capable of producing heterologous antibodies and transgenic non-human animals having inactivated endogenous immunoglobulin genes. Endogenous immunoglobulin genes are suppressed by antisense polynucleotides and/or by antiserum directed against endogenous immunoglobulins. Heterologous antibodies are encoded by immunoglobulin genes not normally found in the genome of that species of non-human animal. One or more transgenes containing sequences of unrearranged heterologous human immunoglobulin heavy chains are introduced into a non-human animal thereby forming a transgenic animal capable of functionally rearranging transgenic immunoglobulin sequences and producing a repertoire of antibodies of various isotypes encoded by human immunoglobulin genes. Such heterologous human antibodies are produced in B-cells which are thereafter immortalized, e.g., by fusing with an immortalizing cell line such as a myeloma or by manipulating such B-cells by other techniques to perpetuate a cell line capable of producing a monoclonal heterologous, fully human antibody homolog.

Yet another preferred binding agent which may block VLA antigens in the method of the invention is a humanized antibody homolog having the capability of binding to a VLA protein. Following the early methods for the preparation of chimeric antibodies, a new approach was described in EP 0239400 (Winter et al.) whereby antibodies are altered by substitution of their complementarity determining regions (CDRs) for one species with those from another. This process may be used, for example, to substitute the CDRs from human heavy and light chain Ig variable region domains with alternative CDRs from murine variable region domains. These altered Ig variable regions may subsequently be combined with human Ig constant regions to created antibodies which are totally human in composition except for the substituted murine CDRs. Such CDR-substituted antibodies would be predicted to be less likely to elicit an immune response in humans compared to chimeric antibodies because the CDR-substituted antibodies contain considerably less non-human components. The process for humanizing monoclonal antibodies via CDR "grafting" has been termed "reshaping". (Riechmann et al., 1988 Nature 332: 323–327, "Reshaping human antibodies for therapy"; Verhoeyen et al., 1988, Science 239: 1534–1536, "Reshaping of human antibodies using CDR-grafting in Monoclonal Antibodies".

Typically, complementarity determining regions (CDRs) of a murine antibody are transplanted onto the corresponding regions in a human antibody, since it is the CDRs (three in antibody heavy chains, three in light chains) that are the regions of the mouse antibody which bind to a specific antigen. Transplantation of CDRs is achieved by genetic engineering whereby CDR DNA sequences are determined by cloning of murine heavy and light chain variable (V) region gene segments, and are then transferred to corresponding human V regions by site directed mutagenesis. In the final stage of the process, human constant region gene segments of the desired isotype (usually gamma I for CH and kappa for CL) are added and the humanized heavy and light chain genes are co-expressed in mammalian cells to produce soluble humanized antibody.

The transfer of these CDRs to a human antibody confers on this antibody the antigen binding properties of the original murine antibody. The six CDRs in the murine antibody are mounted structurally on a V region "framework" region. The reason that CDR-grafting is successful is that framework regions between mouse and human antibodies may have very similar 3-D structures with similar points of attachment for CDRS, such that CDRs can be interchanged. Such humanized antibody homologs may be prepared, as exemplified in Jones et al., 1986 Nature 321: 522–525, "Replacing the complementarity-determining regions in a human antibody with those from a mouse"; Riechmann, 1988, Nature 332:323–327, "Reshaping human antibodies for therapy"; Queen et al., 1989, Proc. Nat. Acad. Sci. USA 86:10029, "A humanized antibody that binds to the interleukin 2 receptor" and Orlandi et al., 1989, Proc. Natl. Acad. Sci. USA 86:3833 "Cloning Immunoglobulin variable domains for expression by the polymerase chain reaction".

Nonetheless, certain amino acids within framework regions are thought to interact with CDRs and to influence overall antigen binding affinity. The direct transfer of CDRs from a murine antibody to produce a humanized antibody without any modifications of the human V region frameworks often results in a partial or complete loss of binding affinity. In a number of cases, it appears to be critical to alter residues in the framework regions of the acceptor antibody in order to obtain binding activity.

Queen et al., 1989, Proc. Nat. Acad. Sci. USA 86: 10029–10033, "A humanized antibody that binds to the interleukin 2 receptor" and WO 90/07861 (Protein Design Labs Inc.) have described the preparation of a humanized antibody that contains modified residues in the framework regions of the acceptor antibody by combining the CDRs of a murine mAb (anti-Tac) with human immunoglobulin framework and constant regions. They have demonstrated one solution to the problem of the loss of binding affinity that often results from direct CDR transfer without any modifications of the human V region framework residues; their solution involves two key steps. First, the human V framework regions are chosen by computer analysts for optimal protein sequence homology to the V region framework of the original murine antibody, in this case, the anti-Tac MAb. In the second step, the tertiary structure of the murine V region is modelled by computer in order to visualize framework amino acid residues which are likely to interact with the murine CDRs and these murine amino acid residues are then superimposed on the homologous human framework. Their approach of employing homologous human frameworks with putative murine contact residues resulted in humanized antibodies with similar binding affinities to the original murine antibody with respect to antibodies specific for the interleukin 2 receptor (Queen et al., 1989 [supra]) and also for antibodies specific for herpes simplex virus (HSV) (Co. et al., 1991, Proc. Nat. Acad. Sci. USA 88: 2869–2873, "Humanised antibodies for antiviral therapy".

According to the above described two step approach in WO 90/07861, Queen et al. outlined several criteria for designing humanized immunoglobulins. The first criterion is to use as the human acceptor the framework from a particular human immunoglobulin that is usually homologous to the non-human donor immunoglobulin to be humanized, or to use a consensus framework from many human antibodies. The second criterion is to use the donor amino acid rather than the acceptor if the human acceptor residue is unusual and the donor residue is typical for human sequences at a specific residue of the framework. The third criterion is to use the donor framework amino acid residue rather than the acceptor at positions immediately adjacent to the CDRS One may use a different approach (see Tempest, 1991, Biotechnology 9: 266–271, "Reshaping a human monoclonal antibody to inhibit human respiratory syncytial virus infection in vivo" ) and utilize, as standard, the V region frameworks derived from NEWM and REI heavy and light chains respectively for CDR-grafting without radical introduction of mouse residues. An advantage of using the Tempest et al., 1991 approach to construct NEWM and REI based humanized antibodies is that the 3dimensional structures of NEWM and REI variable regions are known from x-ray crystallography and thus specific interactions between CDRs and V region framework residues can be modeled.

Regardless of the approach taken, the examples of the initial humanized antibody homologs prepared to date have shown that it is not a straightforward process. However, even acknowledging that such framework changes may be necessary, it is not possible to predict, on the basis of the available prior art, which, if any, framework residues will need to be altered to obtain functional humanized antibodies of the desired specificity. Results thus far indicate that changes necessary to preserve specificity and/or affinity are for the most part unique to a given antibody and cannot be predicted based on the humanization of a different antibody.

Subjects

The subject treatments are effective on both human and animal subjects afflicted with these conditions. Animal subjects to which the invention is applicable extend to both domestic animals and livestock, raised either as pets or for commercial purposes. Examples are dogs, cats, cattle, horses, sheep, hogs and goats.

Pharmaceutical Preparations

In the methods of the invention the anti-VLA antibodies may be administered parenterally. The term "parenteral" as used herein includes subcutaneous, intravenous, intramuscular, intra-articular, intra-synovial, intrasternal, intrathecal, intrahepatic, intralesional and intracranial injection or infusion techniques.

The antibody homologs are preferably administered as a sterile pharmaceutical composition containing a pharmaceutically acceptable carrier, which may be any of the numerous well known carriers, such as water, saline, phosphate buffered saline, dextrose, glycerol, ethanol, and the like, or combinations thereof. The compounds of the present invention may be used in the form of pharmaceutically acceptable salts derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, tris (hydroxymethyl)methylamine and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The pharmaceutical compositions of this invention comprise any of the compounds of the present invention, or pharmaceutically acceptable derivatives thereof, together with any pharmaceutically acceptable carrier. The term "carrier" as used herein includes acceptable adjuvants and vehicles. Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically-acceptable oils, such as olive oil or castor oil, especially in their polyoxyethylated versions.

The pharmaceutical compositions of this invention may be given orally. If given orally, they can be administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

In addition to the direct topical application of the preparations they can be topically administered by other methods, for example, encapsulated in a temperature and/or pressure sensitive matrix or in film or solid carrier which is soluble in body fluids and the like for subsequent release, preferably sustained-release of the active component. As appropriate compositions for topical application there may be cited all compositions usually employed for topically administering therapeutics, e.g., creams, genies, dressings, shampoos, tinctures, pastes, ointments, salves, powders, liquid or semi-liquid formulation and the like. Application of said compositions may be by aerosol e.g. with a propellent such as nitrogen carbon dioxide, a freon, or without a propellent such as a pump spray, drops, lotions, or a semisolid such as a thickened composition which can be applied by a swab. In particular compositions, semisolid compositions such as salves, creams, pastes, genies, ointments and the like will conveniently be used.

Particular compositions for use in the method of the present invention are those wherein the anti-VLA antibody is formulated in vesicles such as liposome-containing compositions. Liposomes are vesicles formed by amphiphatic molecules such as polar lipids, for example, phosphatidyl cholines, ethanolamines and serines, sphingomyelins, cardiolipins, plasmalogens, phosphatidic acids and cerebiosides. Liposomes are formed when suitable amphiphathic molecules are allowed to swell in water or aqueous solutions to form liquid crystals usually of multilayer structure comprised of many bilayers separated from each other by aqueous material (also referred to as coarse liposomes). Another type of liposome known to be consisting of a single bilayer encapsulating aqueous material is referred to as a unilamellar vesicle. If watersoluble materials are included in the aqueous phase during the swelling of the lipids they become entrapped in the aqueous layer between the lipid bilayers.

A particularly convenient method for preparing liposome formulated forms of anti-VLA antibodies is the method described in EP-A-253,619, incorporated herein by reference. In this method, single bilayered liposomes containing encapsulated active ingredients are prepared by dissolving the lipid component in an organic medium, injecting the organic solution of the lipid component under pressure into an aqueous component while simultaneously mixing the organic and aqueous components with a high speed homogenizer or mixing means, whereupon the liposomes are formed spontaneously. The single bilayered liposomes containing the encapsulated active ingredient can be employed directly or they can be employed in a suitable pharmaceutically acceptable carrier for topical administration. The viscosity of the liposomes can be increased by the addition of one or more suitable thickening agents such as, for example xanthan gum, hydroxypropyl cellulose, hydroxypropyl methylcellulose and mixtures thereof. The aqueous component may consist of water alone or it may contain electrolytes, buffered systems and other ingredients, such as, for example, preservatives. Suitable electrolytes which can be employed include metal salts such as alkali metal and alkaline earth metal salts. The preferred metal salts are calcium chloride, sodium chloride and potassium chloride. The concentration of the electrolyte may vary from zero to 260 mM, preferably from 5 mM to 160 mM. The aqueous component is placed in a suitable vessel which can be adapted to effect homogenization by effecting great turbulence during the injection of the organic component. Homogenization of the two components can be accomplished within the vessel, or, alternatively, the aqueous and organic components may be injected separately into a mixing means which is located outside the vessel. In the latter case, the liposomes are formed in the mixing means and then transferred to another vessel for collection purpose.

The organic component consists of a suitable non-toxic, pharmaceutically acceptable solvent such as, for example ethanol, glycerol, propylene glycol and polyethylene glycol, and a suitable phospholipid which is soluble in the solvent. Suitable phospholipids which can be employed include lecithin, phosphatidylcholine, phosphatydylserine, phosphatidylethanol-amine, phosphatidylinositol, lysophosphatidylcholine and phospha-tidyl glycerol, for example. Other lipophilic additives may be employed in order to selectively modify the characteristics of the liposomes. Examples of such other additives include stearylamine, phosphatidic acid, tocopherol, cholesterol and lanolin extracts.

In addition, other ingredients which can prevent oxidation of the phospholipids may be added to the organic component. Examples of such other ingredients include tocopherol, butylated hydroxyanisole, butylated hydroxytoluene, ascorbyl palmitate and ascorbyl oleate. Preservatives such a benzoic acid, methyl paraben and propyl paraben may also be added.

Apart from the above-described compositions, use may be made of covers, e.g. plasters, bandages, dressings, gauze pads and the like, containing an appropriate amount of an anti-VLA antibody therapeutic. In some cases use may be made of plasters, bandages, dressings, gauze pads and the like which have been impregnated with a topical formulation containing the therapeutic formulation.

The pharmaceutical compositions of this invention may also be administered by nasal aerosol or inhalation through the use of a nebulizer, a dry powder inhaler or a metered dose inhaler. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

According to another embodiment compositions containing a compound of this invention may also comprise an additional agent selected from the group consisting of corticosteroids, antiinflammatories, immunosuppressants, antimetabolites, and immunomodulators. Specific compounds within each of these classes may be selected from any of those listed under the appropriate group headings in "Comprehensive Medicinal Chemistry", Pergamon Press, Oxford, England, pp. 970–986 (1990), the disclosure of which is herein incorporated by reference. Also included within this group are compounds such as theophylline, sulfasalazine and aminosalicylates (antiinflammatories); cyclosporin, FK-506, and rapamycin (immunosuppressants); cyclophosphamide and methotrexate (antimetabolites); steroids (inhaled, oral or topical) and interferons (immunomodulators).

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is co-administered.

The dosage and dose rate of the compounds of this invention effective to produce the desired effects will depend on a variety of factors, such as the nature of the inhibitor, the size of the patient, the goal of the treatment, the nature of the pathology to be treated, the specific pharmaceutical composition used, and the judgment of the treating physician. Dosage levels of between about 0.001 and about 100 mg/kg body weight per day, preferably between about 0.1 and about 50 mg/kg body weight per day of the active ingredient compound are useful. Most preferably, the antibody homologs will be administered at a dose ranging between about 0.1 mg/kg body weight/day and about 20 mg/kg body weight/day, preferably ranging between about 0.1 mg/kg body weight/day and about 10 mg/kg body weight/day and at intervals of every 1–14 days. Preferably, an antibody composition is administered in an amount effective to provide a plasma level of antibody of at least 1 ug/ml.

Persons having ordinary skill in the art can readily test if an antagonist of the invention is having it intended effect. For instance, cells contained in a sample of the individual's epithelium are probed for the presence of the agent in vitro (or ex vivo) using a second reagent to detect the administered agent. For example, this may be a fluorochrome labelled antibody specific for the administered agent which is then measured by standard FACS (fluorescence activated cell sorter) analysis. Alternatively, presence of the administered agent is detected in vitro (or ex vivo) by the inability or decreased ability of the individual's cells to bind the same agent which has been itself labelled (e.g., by a fluorochrome). The preferred dosage should produce detectable coating of the vast majority of hedgehog-positive cells. Preferably, coating is sustained in the case of an antibody homolog for a 1–14 day period.

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, Molecular Cloning: A Laboratory Manual, 2nd edition. (Sambrook, Fritsch and Maniatis, eds.), Cold Spring Harbor Laboratory Press, 1989; DNA Cloning, Volumes I and II (D. N. Glover, ed), 1985; Oligonucleotide Synthesis, (M. J. Gait, ed.), 1984; U.S. Pat. No. 4,683,195 (Mullis et al.,); Nucleic Acid Hybridization (B. D. Hames and S. J. Higgins, eds.), 1984; Transcription and Translation (B. D. Hames and S. J. Higgins, eds.), 1984; Culture of Animal Cells (R. I. Freshney, ed). Alan R. Liss, Inc., 1987; Immobilized Cells and Enzymes, IRL Press, 1986; A Practical Guide to Molecular Cloning (B. Perbal), 1984; Methods in Enzymology, Volumes 154 and 155 (Wu et al., eds), Academic Press, New York; Gene Transfer Vectors for Mammalian Cells (J. H. Miller and M. P. Calos, eds.), 1987, Cold Spring Harbor Laboratory; Immunochemical Methods in Cell and Molecular Biology (Mayer and Walker, eds.), Academic Press, London, 1987; Handbook of Experiment Immunology, Volumes I–IV (D. M. Weir and C. C. Blackwell, eds.), 1986; Manipulating the Mouse Embryo, Cold Spring Harbor Laboratory Press, 1986.

The following Examples are provided to illustrate the present invention, and should not be construed as limiting thereof.

EXAMPLES

Example 1

Treatment of Animals

Male C57/BL6 mice weighing 28–30 g, were housed in plastic cages in groups of 4 in facilities approved by the American Association for Accreditation of Laboratory Animal Care. The animals were allowed to acclimate for one week to laboratory conditions prior to starting the experiments. They had access to Rodent Laboratory Chow 5001 (Purina Mills, Inc., St. Louis, Mo.) and water ad libitum and housed in a room which gets filtered air and has 12 hr light/12 hr dark cycle. Mice were assigned into the following groups:

| GROUP | TREATMENT |
|---|---|
| A | Saline + Phosphate buffered saline |
| B | Saline + Ha4/8 control IgG |
| C | Bleomycin + Ha4/8 control IgG |
| D | Bleomycin + Ha31/8 (hamster anti-$\alpha$1 $\beta$1 rat integrin antibody) |
| E | Bleomycin + Ha1/29 (hamster anti-$\alpha$2 $\beta$1 rat integrin antibody) |

Bleomycin sulfate was dissolved in pyrogen free sterile isotonic saline just before intratracheal (IT) instillation. Under methoxyflurane anaesthesia mice in appropriate groups received by intratracheal administration either 100 $\mu$l of sterile isotonic solution or 0.08 units of bleomycin solution in 100 $\mu$l. Antibodies (4 mg/kg) were administered by intraperitoneal injection to mice in appropriate groups three times a week for 21 days post installation. Thereafter, the animals in each group were killed by an overdose of sodium pentobarbital (100–125 mg/kg ip) and their lungs processed for bronchoalveolar lavage, biochemical and histopathological studies.

Monoclonal Antibodies

Ha31/8 (hamster anti-rat $\alpha$1$\beta$1 integrin IgG); Ha1/29 (hamster anti-rat $\alpha$2 $\beta$1 integrin IgG); and Ha4/8 (hamster anti-rat control IgG) are described in Mendrick and Kelly, Lab. Invest. 69:690–702 (1993); Mendrick et al, Lab. Invest. 72:367–375 (1995), and commercially available (Pharmingen, San Diego, Calif.).

Determination of Total Cell Number and Protein Levels in Broncoalveolar Lavage

After cannulation of the trachea the lungs were lavaged with 5 ml of isotonic saline, given in five aliquots of 1 ml. The saline was administered with a syringe through the cannula, the chest wall was gently massaged, and the fluid was withdrawn. The fluid was centrifuged at 1500 g for 20 minutes at 4 degree C., and resusended in isotonic saline solution. The protein content for the supernatant from broncoalveolar lavage specimens was determined by a method of Lowry et al., J Biol. Chem. 1193: 265–275 (1951), with bovine serume albumin as a standard. Total leukocyte count of cells in suspension was determined in a Coulter Counter (Coulter Electronics, Hialeah, Fla.).

Determination of Hydoxyproline

The lungs of animals used for biochemical studies were perfused in situ via the right ventricle with ice-cold isotonic saline to wash out blood from the pulmonary vasculature through an opening in the left auricle. The lung lobes were quickly dissected free of non-parenchymal tissue, dropped in liquid nitrogen for quick freezing and then stored at $-80°$ C. The frozen lungs were later thawed and homogenized in 0.1 M KCl, 0.02 M Tris buffer (pH 7.6) with a Polytron homogenizer. Hydroxyproline content of the lung homogenate as a measure of collagen content was quantitated by the techniques of Woessner, Arch. Biochem. Biophys. 93: 440–447 (1961).

Results

In this study, we tested the hypothesis that neutralizing antibody for integrin $\alpha$1$\beta$1 (anti$\alpha$1$\beta$1) or integrin $\alpha$2$\beta$1 (anti$\alpha$2$\beta$1) may reduce bleomycin (BL)-induced lung fibrosis in vivo. Male C57/BL6 mice were intratraceally (IT) injected saline (SA) or BL at 0.08 U in 0.1 ml followed by intraperitoneal (IP) injection of the antibody (100 $\mu$g in 0.2 ml) three times a week. Twenty-one days after the IT instillation, mice were killed for bronchoalveolar lavage (BAL), biochemical and histopathological analysis.

Results:

| Group (n) | Treatment (IT + IP) | Hydroxyproline ($\mu$g/lung) | Total BAL cells ($\times 10^{-3}$/lung) | BAL protein ($\mu$g/lung) |
|---|---|---|---|---|
| A(12) | SA + PBS | 231 ± 15 | 2.2 ± 0.14 | 171 ± 21 |
| B(10) | SA + IgG | 225 ± 21 | 2.3 ± 0.24 | 167 ± 24 |
| C(9) | BL + IgG | 371 ± 42* | 6.7 ± 0.99* | 1079 ± 292* |
| D(11) | BL + anti$\alpha$1$\beta$1 | 230 ± 20 | 6.5 ± 1.17* | 1238 ± 244* |
| E(10) | BL + anti$\alpha$2$\beta$1 | 221 ± 14 | 4.2 ± 0.72 | 945 ± 184* |

*Significantly higher than other group

Lung histopathology showed fibrotic lesions in C group of mice, but lungs from D and E groups indicated somewhat reduced fibrosis compared to C group. Our data demonstrated that treatment with anti$\alpha$1$\beta$1 or anti$\alpha$2$\beta$1 antibody reduced BL-induced lung collagen accumulation in mice. However, treatment with either antibody did not affect BL-induced increases in the BAL cell number and protein level, except for anti$\alpha$2$\beta$1 which reduced the total BAL cells. It is concluded that integrins $\alpha$1$\beta$1 and $\alpha$1$\beta$2 play important roles in BL-induced pulmonary fibrosis and the use of anti$\alpha$1$\beta$1 or anti$\alpha$2$\beta$2 antibody has great antifibrotic potential in vivo.

Example 2

Histopathological Study

After lung lavage, the thoracic cavity was opened and the heart and lungs were removed en bloc. The lungs were instilled with a 1% glutaraldehyde-paraformaldehyde fixative in 0.12M cacodylate buffer at 400 m Osm at 30 cm $H_2O$ presure. The lungs are fixed via this pressure for about 2 hours and then stored in fixative with the tracheas occluded. Before embedding, the lung was isolated from the heart and all non-pulmonary tissue by blunt dissection and removed. Blocks of tissue were cut from at least two sagittal slabs (2–3 mm thick) from the right cranial, right caudal, and left lung lobes of each lung. Each block was cut with about a 1 $cm^2$ face. The blocks were dehydrated in a graded series of ethanol and embedded in paraffin. Sections (5 μm thick) were cut from the paraffin blocks and stained with haematoxylin and eosin for histological evaluations.

Data Analysis and Interpretation

The data are analyzed in terms of average values with their standard deviations and standard errors of means. Student's t-test, chi-square distributions, correlation coefficient, analysis of variance (ANOVA) and multiple comparison test will be applied to judge the significance of differences between the control and treatment groups using a computer based statistical package (SAS/STAT Guide, 6th Ed. Cary, N.C. pp. 183–260 (1985)).

Histopathological Examination of Lungs

Histopathological examination of lungs was carried out on mice sacrificed at 21 days after intratracheal instillation of saline or bleomycin. The mice treated with saline and control IgG (Group B) had no visible lesions and displayed interalveolar septa with a normal thin appearance. In contrast, mice treated with bleomycin and control IgG (Group C) had lesions varying from multifocal locations in proximal acini to a diffuse distribution that occasionally involved the pleura. In diffuse lesions, alveolar spaces were often obliterated by organized connective tissue and fibrotic lesions. In the multifocal lesion interalveolar septa were thickened and lined by hypertrophied and hyperplastic cuboidal epithelial cells and abundant airway inflammatory cells. The lungs of mice treated with bleomycin and either anti-alpha1 (Group D) and alpha2 (Group E) integrin antibodies appeared more like those in Group B. Group D and E animals exhibited only a limited number of fibrotic lesions, with mild multifocal septal thickening and small aggregates of mononuclear cells.

Example 3

Cloning and mutagenesis of the α1-I domain. Human and rat α1β1 integrin I domain sequences were amplified from full length cDNAs (Kern, et al. (1994) *J. Biol. Chem.* 269, 22811–22816; Ignatius et al. (1990) *J. Cell Biol.* 111, 709–720) by the polymerase chain reaction (PCR) (PCR CORE Kit; Boehringer Mannheim, GmbH Germany), using either human specific (5'-CAGGATCCGTCAGCC-CCACATTTCAA-3' (SEQ ID NO:1) [forward]; 5'-TCCTCGAGGGCTTGCAGGGCAAATAT-3' (SEQ ID NO:2) [reverse]) or rat specific (5'-CAGGATCCGTCAGTCCTACATTTCAA-3' (SEQ ID NO:3) [forward]; 5'-TCCTCGAGCGCTTCCAAAG-CGAATAT-3' (SEQ ID NO:4) [reverse]) primers. The resulting PCR amplified products were purified, ligated into pGEX4t-i (Pharmacia), and transformed into competent DH5α cells (Life Technologies). Ampicillin resistant colonies were screened for the expression of the ~45 kDa glutathione S-transferase-I domain fusion protein. The sequences from inserts of plasmid DNA of clones that were selected for further characterization were confirmed by DNA sequencing.

A rat/human chimeric α1-I domain (RΔH) was generated (MORPH Mutagenesis kit; 5 prime-3 prime), exchanging the rat residues G92, R93, Q94, and L97 (box in FIG. 4A) for the corresponding human residues, V, Q, R, and R, respectively. Clones harboring the RΔH I domain were identified by the loss of a diagnostic Stu 1 restriction enzyme site, and the inserts confirmed by DNA sequencing. The amino acid sequence of the human α1-I domain is shown in FIG. 5.

Example 4

Generation of mAbs specific to the -α1 I domain. Monoclonal antibodies have proved to be very useful probes in studying the relationship between structure and function of integrin subunits. For example, mAbs were used extensively to study regions of the β1 subunit associated with an activated conformation (Qu, A., and Leahy, D. J. (1996) *Structure* 4, 931–942). Thus, to identify potential probes for conformational changes of the α1-I domain, we generated a panel of mAbs to the human α1-I domain.

Generation of anti-α1 I domain Monoclonal Antibodies. Female Robertsonian mice (Jackson Labs) were immunized intraperitoneally (i.p.) with 25 μg of purified human α1β1 (Edwards et al. (1995) *J. Biol. Chem.* 270, 12635–12640) emulsified with complete Fruend's adjuvant (LifeTechnologies). They were boosted three times i.p. with 25 μg of α1β1 emulsified with incomplete Freunds's adjuvant (LifeTechnologies). The mouse with the highest anti-α1-I domain titer was boosted i.p. with 100 μg of α1β1 three days prior to fusion, and intravenously with 50 μg of α1β1 one day prior to fusion. Spleen cells were fused with FL653 myeloma cells at a 1:6 ratio and were plated at 100,000 and 33,000 per well into 96 well tissue culture plates.

Supernatants were assessed for binding to the α1β1 integrin by single color FACS. Prior to FACS analysis, supernatants were incubated with untransfected K562 cells to eliminate IgG that bound solely to the β subunit. Subsequently, 3–5×$10^4$ K562 cells transfected with the α1 integrin subunit (K562–α1) suspended in FACS buffer (1% fetal calf serum (FCS) in PBS containing 0.5% $NaN_3$) were incubated with supernatant for 45 minutes at 4° C., washed and incubated with anti-mouse IgG conjugated to phycoerythrin. After washing twice with FACS buffer, cells were analyzed in a Becton Dickinson Flow Cytometer.

Supernantants from the resulting hybridomas were screened for binding to the α1-I domain. Briefly, 50 μl of 30 μg/ml human α1-I domain-GST fusion in PBS was coated onto wells of a 96-well plate (Nunc) overnight at 4° C. The plates were washed with PBS, blocked with 1% BSA in PBS and the hybridoma supernatant was incubated with the I domain at room temperature for 1 hour. After extensive washing with PBS containing 0.03% Tween 20, alkaline phosphatase linked anti-mouse IgG (Jackson ImmunoResearch) was added for an additional hour. After a final wash, 1 mg/ml p-nitrophenylphosphate (PNPP) in 0.1 M glycine, 1 mM $ZnCl_2$, and 1 mM $MgCl_2$ was added for 30 minutes at room temperature, and the plates were read at O.D. 405.

Selected supernatants were tested for their ability to inhibit K562-α1 dependent adhesion to Collagen IV. K562-α1 cells were labeled with 2 mM 2',7' (bis-2-carboxyethyl-5 and 6) carboxyfluorescein penta acetoxymethylester (BCECF; Molecular Probes) in DMEM containing 0.25% BSA at 37° C. for 30 minutes. Labeled cells were washed with binding buffer (10 mM Hepes, pH 7.4; 0.9% NaCl; and 2% glucose) and resuspended in binding buffer plus 5 mM $MgCl_2$ at a final concentration of 1×$10^6$ cells/ml. 50 μl of supernatant was incubated with an equal volume of 2×$10^5$ K562–α1 cells in wells of a 96 well plate. The plate was then centrifuged and the supernatants removed. Cells were resuspended in binding buffer and transferred to wells of a collagen-coated plate and incubated for 1 hour at 37° C. Following incubation, the non-adherent cells were removed by washing three times with binding buffer. Attached cells were analyzed on a Cytofluor (Millipore).

Figure 2A:
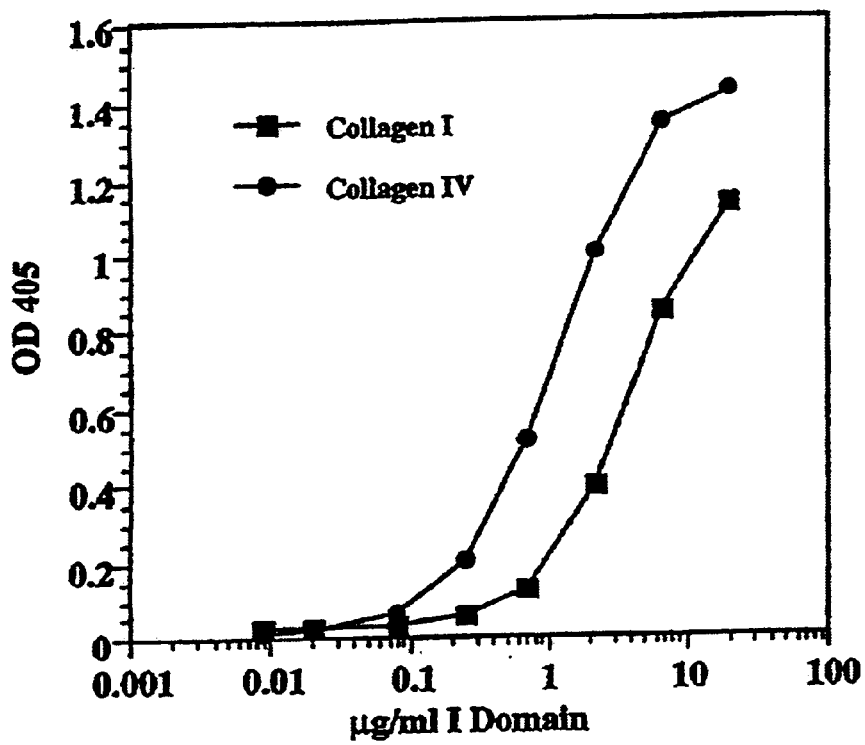
FIG. 2A–FIG. 2C. Identification of a blocking mAb to the $\alpha1$-I domain.
Figure 2B:
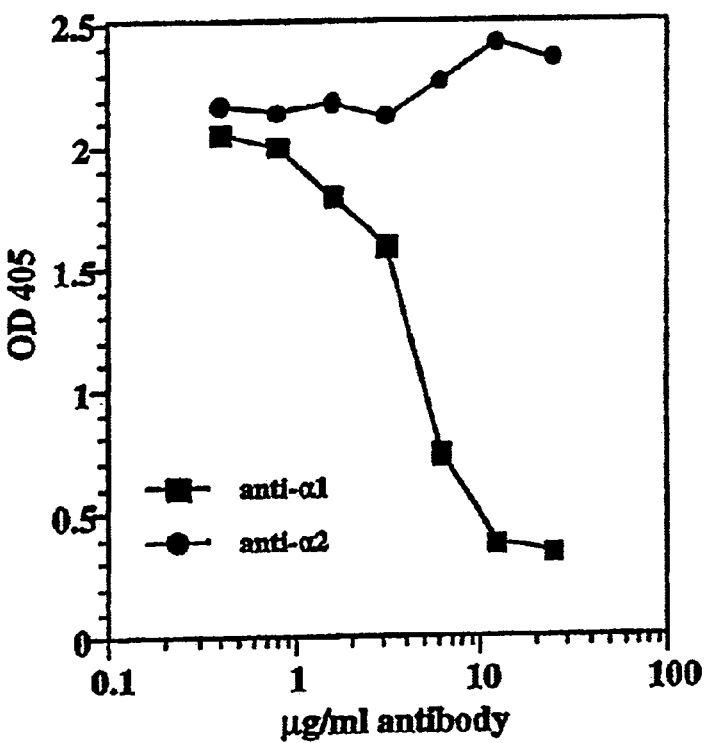
Figure 2C:
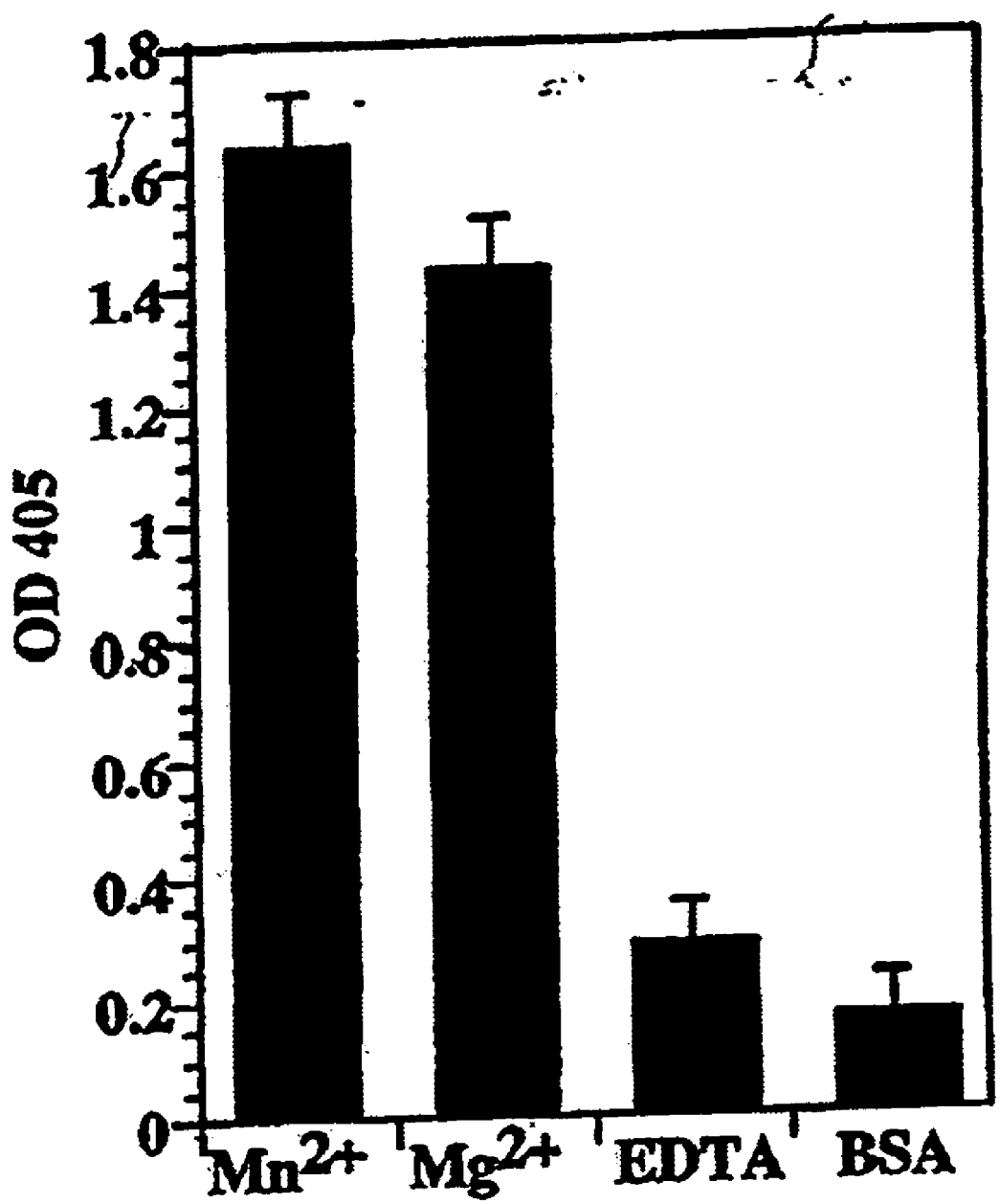

We initially identified 19 hybridomas, the supernatants of which bound to human leukemia K562 cells expressing the α1β1 integrin (K562–α1) and to the α1-I domain. The immunoglobulins were purified from each of these hybridomas and tested for the ability to block either K562-α1 or α1-I domain binding to collagen IV. The mAbs fall into two classes: those that block and those that do not block α1β1 function. For example, while the mAbs produced by clones AEF3, BGC5 and AJH10 bind the α1-I domain (FIG. 2A, data not shown for BGC5), only mAb AJH10 inhibits α1-I domain-dependent (FIG. 2B) or K562–α1 (FIG. 2C) adhesion to collagen IV.

Sequencing of the Complementarity Determining Regions. To establish the clonal origin of this panel of mAbs, we amplified by PCR and sequenced the CDRs from 12 of the 19 antibodies (data not shown).

2 μg of mRNA, isolated from $10^7$ hybridomas (FastTrack mRNA isolation kit, Invitrogen), was reverse transcribed (Ready-To-Go You Prime First Strand Kit, Pharmacia Biotech) using 25 pM each of the following primers: heavy chain VH1FOR-2 (Michishita et al. (1993) *Cell* 72, 857–867); light chain, VK4FOR, which defines four separate oligos (Kern et al. (1994) *J. Biol. Chem.* 269, 22811–22816). For each hybridoma, heavy and light chains were amplified in four separate PCR reactions using various combination of the following oligos: 1) Heavy chain: VH1FR1K (Kamata et al. (1995) *J. of Biol. Chem.* 270, 12531–12535), VH1BACK, VH1BACK (Baldwin et al. (1998) *Structure* 6, 923–935), $V_H$fr1a, $V_H$fr1b, $V_H$fr1e, $V_H$fr1f, $V_H$fr1g (Ignatius et al. (1990) *J. Cell Biol.* 111, 709–720), or VH1FOR-2 (Michishita, M., Videm, V., and Arnaout, M. A. (1993) *Cell* 72, 857–867); 2) Light chain: VK1BACK (Baldwin et al. (1998) *Structure* 6, 923–935), VK4FOR, VK2BACK oligos (Kern et al. (1994) *J. Biol. Chem.* 269, 22811–22816), or $V_K$fr1a, $V_H$fr1c, $V_H$fr1e, $V_H$fr1f (Ignatius et al. (1990) *J. Cell Biol.* 111, 709–720). Products were amplified (5 min at 95° C., 50 cycles of 1 min at 94° C., 2 min at 55° C., 2 min at 72° C., and a final cycle of 10 min at 72° C.), gel purified (QIAquick, Qiagen), and sequenced directly using various of the listed oligos on an ABI 377 Sequencer.

Sequences from clones producing function-blocking mAbs were nearly identical across all the complementarity-determining regions (CDRs) and the intervening framework regions suggesting that these hybridomas are clonally related.

Example 5

Immunoblotting and FACS Analysis. Sequences of the variable regions of the non-blocking antibodies were markedly different from the clonally related family of sequences found for the blocking antibodies. As the blocking antibodies appear to originate from a single clone, we chose one (AJH10) to characterize further.

Immunoblotting The smooth muscle cell layer dissected from sheep aorta, and K562-α1 cells were extracted with 1% Triton X-100 in 50 mM Hepes, pH 7.5, 150 mM NaCl, 10 mM phenylmethylsulfonyl flouride (PMSF), 20 μg/ml aprotinin, 10 μg/ml leupeptin, 10 mM ethylenediaminetetraacetic acid (EDTA). Samples were subjected to 4–20% gradient SDS-PAGE, and electroblotted onto nitrocellulose membranes. The blots were blocked with 5% dry milk in TBS; washed in TBS containing 0.03% Tween-20, and incubated with antibodies in blocking buffer containing 0.05% $NaN_3$ for 2 hours. Blots were then washed as before, incubated with horseradish peroxidase conjugated anti-mouse IgG for one hour, washed again and then treated with ECL reagent (Amersham). Blots were then exposed to film (Kodak) for 30 to 60 seconds, and developed.

Figure 3A:
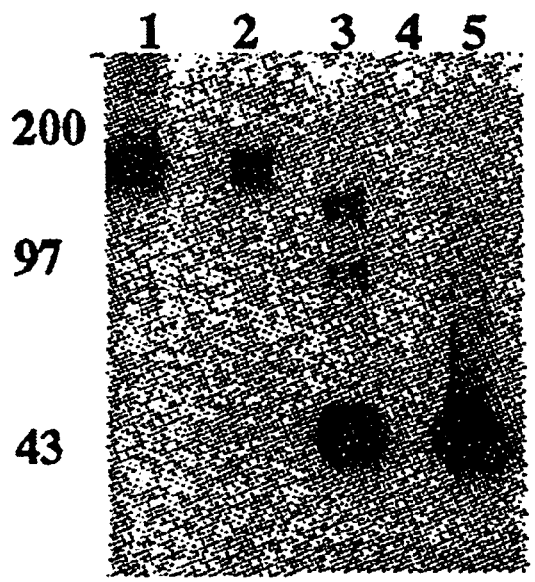
FIG. 3A–FIG. 3B. Species Cross-reactivity of the blocking mAbs. A. Detergents lysates from (1) sheep vascular smooth muscle, (2) human leukemia K562-α1 cells or (3) purified RΔH GST-I domain; (4) Rat GST-α1 I domain; and (5) human GST-α1 I domain were separated by 10–20% SDS-PAGE under non-reducing conditions, and immunoblotted with function-blocking mAb AJH10 (ATCC NO. PTA-3580). Molecular weight markers are shown on the left; non-reduced α1β1 integrin migrates at ~180 kDa; GST-I domain migrates at ~45 kDa.
Figure 3B:
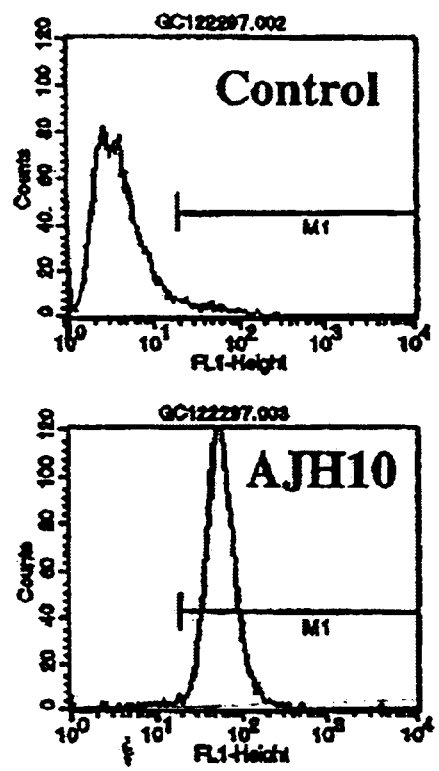

Immunoblotting (FIG. 3A) and FACS analysis (FIG. 3B) demonstrate that AJH10 reacts with human, rabbit, and sheep, but not rat α1β1 integrin suggesting that the blocking mAbs bind to an evolutionarily conserved, linear epitope. The non-blocking mAbs were neither efficient at immunoblotting nor did they react with species other than human.

Example 6

Binding of the α1-I Domain to Collagen is Divalent Cation-dependent

A. Purification of the α1-I domains

The α1-I domains were expressed in *E. coli* as GST (glutathione-S-transferase) fusion proteins containing a thrombin cleavage site at the junction of the sequences. The clarified supernatant from cells lysed in PBS was loaded onto a glutathione Sepharose TM 4B column (Pharmacia) which was washed extensively with PBS. The α1-I domain-GST fusion protein was eluted with 50 mM Tris-HCl, pH 8.0, 5 mM glutathione (reduced). For denaturation studies, the I domain was cleaved with thrombin in 50 mM Tris, pH 7.5, and purified from the GST fusion partner. DTT was added to 2 mM and the sample was loaded on a glutathione Sepharose TM 4B column. The flow-through and wash fractions were pooled and loaded onto a Q Sepharose FF column (Pharmacia). The α1-I domain was eluted with 50 mM Tris HCl, pH 7.5, 10 mM 2-mercaptoethanol, 75 mM NaCl. The purified I domain displayed its predicted mass (Lee et al. (1995) *Structure* 3, 1333–1340, 871 Da) by electrospray ionization-mass spectrometry (ESI-MS), migrated as a single band by SDS-PAGE, and the protein eluted as a single peak of appropriate size by size exclusion chromatography on a Superose TM 6 FPLC column (Pharmacia).

B. Functional Analysis 96 well plates were coated overnight at 4° C. with 1 μg/ml collagen IV (Sigma) or collagen Type I (Collaborative Biomedical), washed with Triton buffer (0.1% Triton X-100; 1 mM $MnCl_2$; 25 mM Tris-HCl; 150 mM NaCl), and blocked with 3% bovine serum albumin (BSA) in 25 mM Tris-HCl; 150 mM NaCl (TBS). Serial dilutions of the α1-I domain-GST fusion protein in TBS containing 1 mM $MnCl_2$ and 3% BSA were incubated on the coated plates at room temperature for 1 hour, and washed in Triton buffer. Bound α1-I domain was detected with serial additions of 10 μg/ml biotinylated anti-GST polyclonal antibody (Pharmacia); ExtrAvidin-horseradish peroxidase (Sigma) diluted 1:3000 in TBS containing 1 mM $MnCl_2$ and 3% BSA, and 1-Step ABTS (2,2'-Azine-di[3-ethylbenzthiazoline sulfonate]; Pierce). Plates were read at O.D. 405 on a microplate reader (Molecular Devices).

Results

Figure 1B:
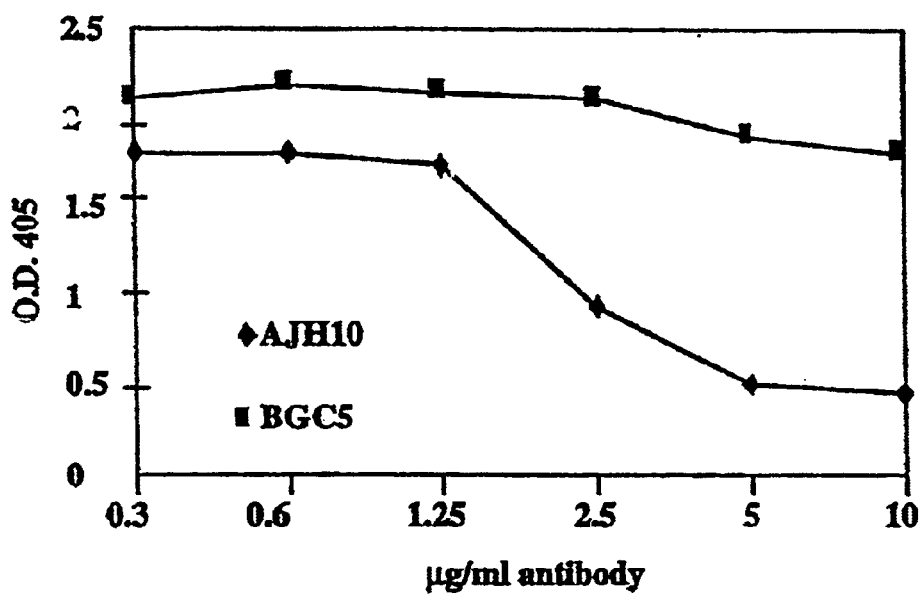
Figure 1C:
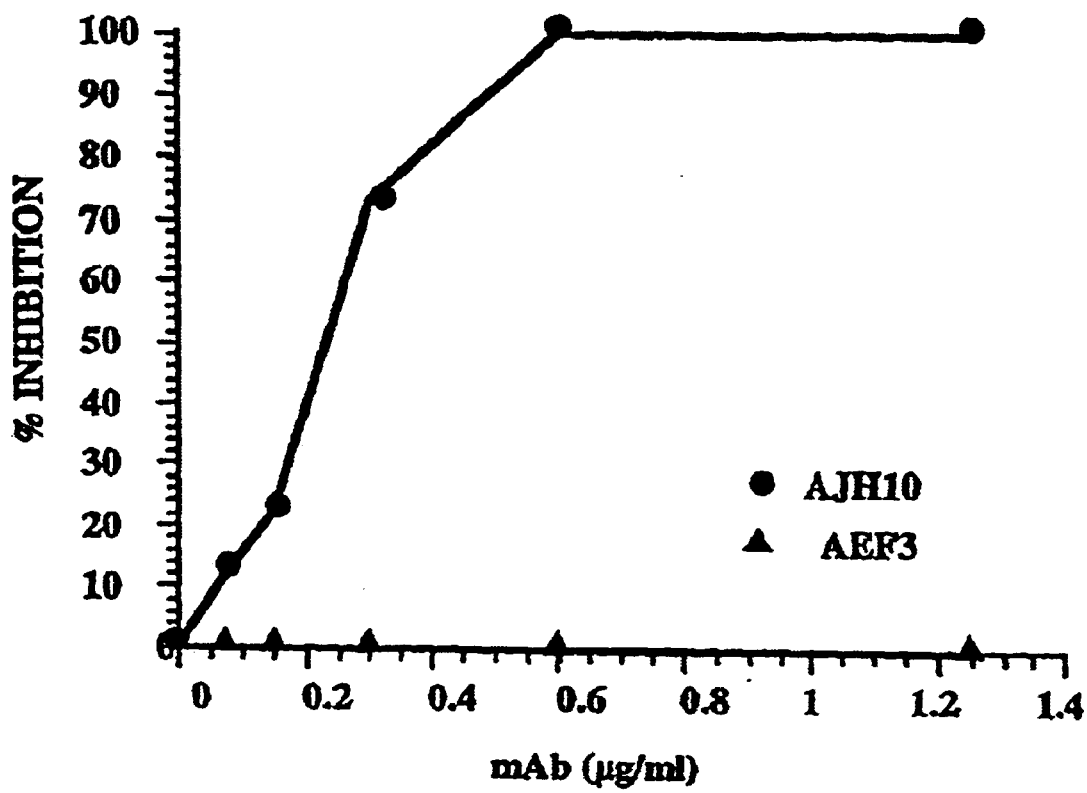

The human and rat (95% identity to human) α1-I domains were expressed in *E. coli* as GST-fusion proteins and purified over glutathione sepharose. Both proteins were examined for binding to collagen I and IV using a variation of an ELISA-based assay previously described (Qu, A., and Leahy, D. J. (1995) *Proc. Natl. Acad. Sci. USA* 92, 10277–10281). The human α1-I domain binds collagen IV with better efficiency than collagen I (FIG. 1A). An antibody specific to the α1-I domain, but not an antibody specific to the α2-I domain (FIG. 1B) abrogated binding to both ligands (data for collagen I is not shown). Both $Mn^{2+}$ and $Mg^{2+}$ stimulated binding, and EDTA reduced binding to background levels (FIG. 1C). No measurable differences in ligand binding were detected between the human and rat α1-I domains suggesting that the sequence differences between species are not functionally relevant (data not shown). Thus, the α1-I domain, specifically, require cation for efficient ligand binding.

Example 7

A Cation-Dependent Epitope Resides near the MIDAS motif. We exploited the observation that AJH10 recognizes the human, but not the rat α1-I domain sequences to map the epitope for the α1β1 function-blocking mAbs. The human and rat sequences differ by only 12 amino acids, 4 of which lie in a stretch of 6 amino acids (aa 91, 96, FIG. 4A) (SEQ ID NOs: 8 and 7, respectively) adjacent to the critical glutamine (FIG. 4A, aa 97) within the MIDAS motif. To test the hypothesis that the 6 amino acid residues, Val-Gln-Arg-Gly-Gly-Arg, comprise the eptitope for the blocking mAbs, we constructed a chimeric I domain (RΔH), which exchanged the rat residues G91, R92 Q93, and L96 for the corresponding human residues, V, Q, R, and R, respectively.

To orient these residues with respect to the MIDAS domain in the tertiary structure of the α1-I domain, we modeled the α1-I domain using the coordinates of the crystal structure of the α2 I domain.

A homology model of the human α1 I-domain was built using the X-ray crystal structure of the human α2 I-domain (Ward et al. (1989) *Nature* 341, 544–546). The model was built using the homology modeling module of Insight II (version 2.3.5; Biosym Technologies). The program CHARMM (Clackson et al. (1991) *Nature* 352, 624–628) was used with the all-hydrogen parameter set 22 with a distant dependent dielectric constant of two times the atom separation distance. We first did 1000 steps of steepest descent minimization with mass-weighted harmonic positional constraints of 1 kcal/(mol Å$^2$) on all atoms of the α1-I domain. This minimization was followed by another 1000 steps of steepest descent and 5000 steps of Adopted-Basis Newton Raphson with constraints of 0.1 kcal/(mol Å$^2$) on the C-α atoms of the α1-I domain to avoid significant deviations from the α2-I domain X-ray crystal structure.

The α1β1 and α2β1 integrin sequences exhibit 51% identity with no insertions or deletions, suggesting that the overall structure of the two I domains will be similar. The metal coordination site is predicted to be the same in the α1-I domain as in the α2-I domain, and the residues that comprise the epitope for the blocking mAbs lie on a loop between helix α3 and helix α4 which contains the threonine within the MIDAS motif critical for cation binding. The α1-I domain model predicts that the amide nitrogen of Q92 (FIG. 4A) hydrogen bonds with the carbonyl group of I33, the residue adjacent to S32. Thus, the loop that contains the epitope may play a functional role in stabilizing the MIDAS region.

Figure 6A:
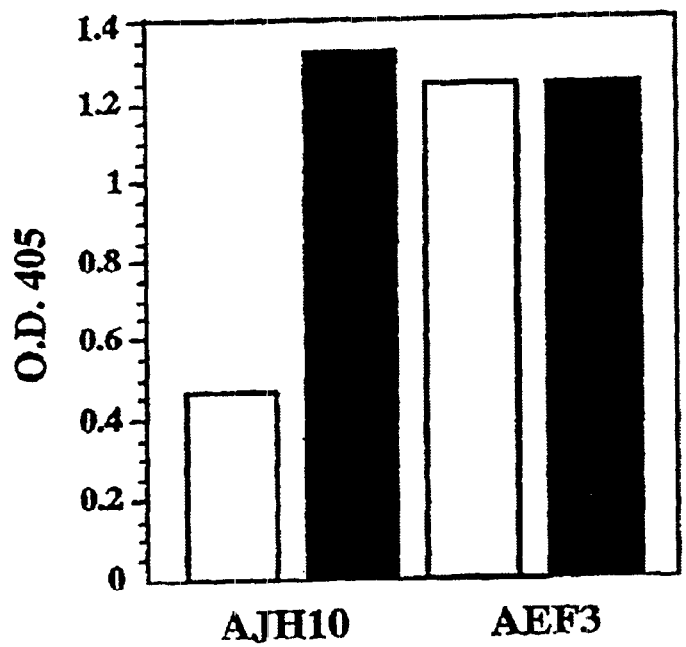
FIG. 6A–FIG. 6B. Cation Stabilizes the Expression of the Epitope.
Figure 6B:
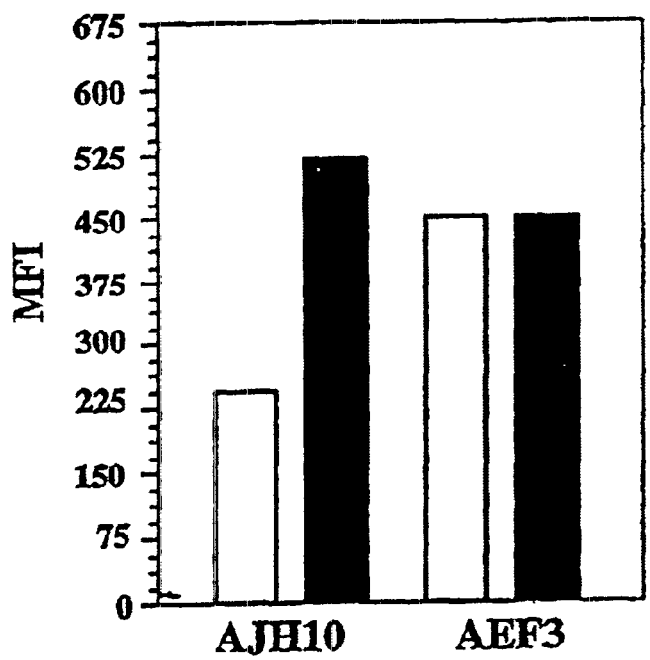

The proximity to and the potential interaction of the loop containing the epitope with the MIDAS motif suggested that the epitope, itself, might be sensitive to the presence of divalent cation. Initial ELISA-based experiments confirmed that binding of AJH10, but not AEF3 (FIG. 6A) to purified α1β1 integrin increases in the presence of cations. Binding of AJH10 to cell surface-expressed α1β1 is also enhanced by the addition of cation (FIG. 6B). To further analyze this observation, we measured the relative binding affinities of the blocking mAbs, in the presence or absence of divalent cations, using a surface plasmon resonance (SPR) biosensor. Monitoring the reversible binding of the mAbs to the recombinant α1-I domain in real time allows the derivation of the association (ka) and dissociation rates (kd), as well as the corresponding apparent dissociation constants ($K_D$). The addition of cation decreased the $K_D$ of blocking mAb AJH10 from 400 to 20 nM (data not shown). The addition of cation had no effect on the $K_D$ of non-blocking, control mAb AEF3 (data not shown). Analysis of the ka and kd associated with binding reveals that the increase in affinity is primarily attributable to a decrease in the rate of dissociation (data not shown). For example, in the absence of cation, AJH10 has a dissociation rate constant of $1.65 \times 10^{-3}$/sec. Addition of $Mn^{2+}$ decreases the dissociation rate constant by a factor of 8 to $2.12 \times 10^{-4}$/sec (data not shown) while increasing the association rate by only a factor of 2($3.9 \times 10^3$ $M^{-1}s^{-1}$ to $8.0 \times 10^3$ $M^{-1}s^{-1}$). Thus, the addition of divalent cation appears to stabilize the epitope rather than unmask a cryptic site, consistent with the proximity of the epitope to the MIDAS region.

Example 8

Cation is required for I domain Stability. One interpretation of the effect $Mn^{2+}$ and $Mg^{2+}$ have on epitope expression is that divalent cations are required to stabilize the MIDAS region, or the entire α1-I domain. Thus, we looked at the stability of the α1-I domain in the presence or absence of cations under denaturing conditions.

Figure 7:
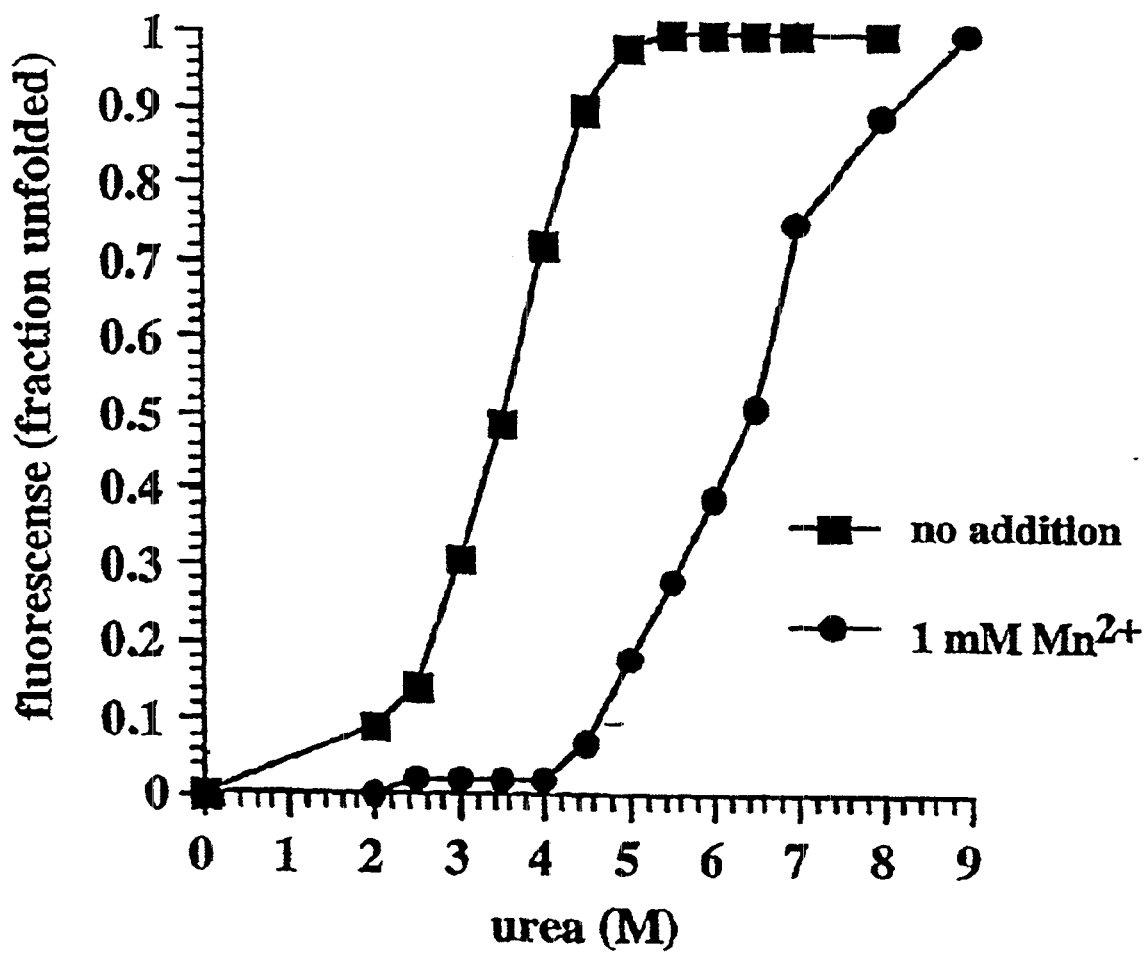
FIG. 7. Denaturation of the α1-I domain by Urea. 0.6 μM rat α1 I domain, in the presence of no cation (squares), or 1 mM $MnCl_2$ (circles) and increasing concentrations of urea were analyzed at 25° C. using an excitation wavelength of 280 nm. Fluorescence data from the emission spectra at 350 nm are plotted as a function of urea concentration and standardized using the change in fluorescence for each of the test conditions as a measure of the total fraction unfolded.

The presence of divalent cations had a stabilizing effect on the α1-I domain structure readily detected by measuring the susceptibility of the protein to denaturation by urea (FIG. 7).

The denaturation of the α1-I domain as a function of urea was measured by fluorescence spectroscopy in an Aminco-Bowman series 2 Luminescence Spectrometer. Samples containing 0.6 μM α1-I domain in 50 mM Tris HCl pH 7.0, 0.15 mM DTT with no addition, 1 mM $CaCl_2$, or 1 mM $MnCl_2$ and with the varying amounts of urea were analyzed at 25° C. using an excitation wavelength of 280 nm. Emission spectra from 300–400 nm were collected. Fluorescence data at 350 nm were plotted as a function of urea and standardized using the change in fluorescence from 0 to 9 M urea for each of the test conditions as a measure of the total fraction folded.

As described above, the denaturation of the α1-I domain was assessed by monitoring the change in intrinsic fluorescence that results from the exposure of buried tryptophan and tyrosine residues to the aqueous environment as the protein unfolds. Denaturation produced both an increase in fluorescence intensity and a red shift in the emission spectrum. The maximal effect was seen at 360 nm where denaturation of the α1-I domain resulted in a greater than 4-fold increase in intrinsic fluorescence intensity. In the absence of divalent cation, the α1-I domain was sensitive to the presence of low concentrations of urea and the amount needed to produce a half maximal change in fluorescence intensity was 3.4 M urea. In the presence of $Mn^{2+}$, half maximal denaturation shifted to 6.3 M urea, indicating a substantial stabilization of the α1-I domain.

Figures 4A, 4B:
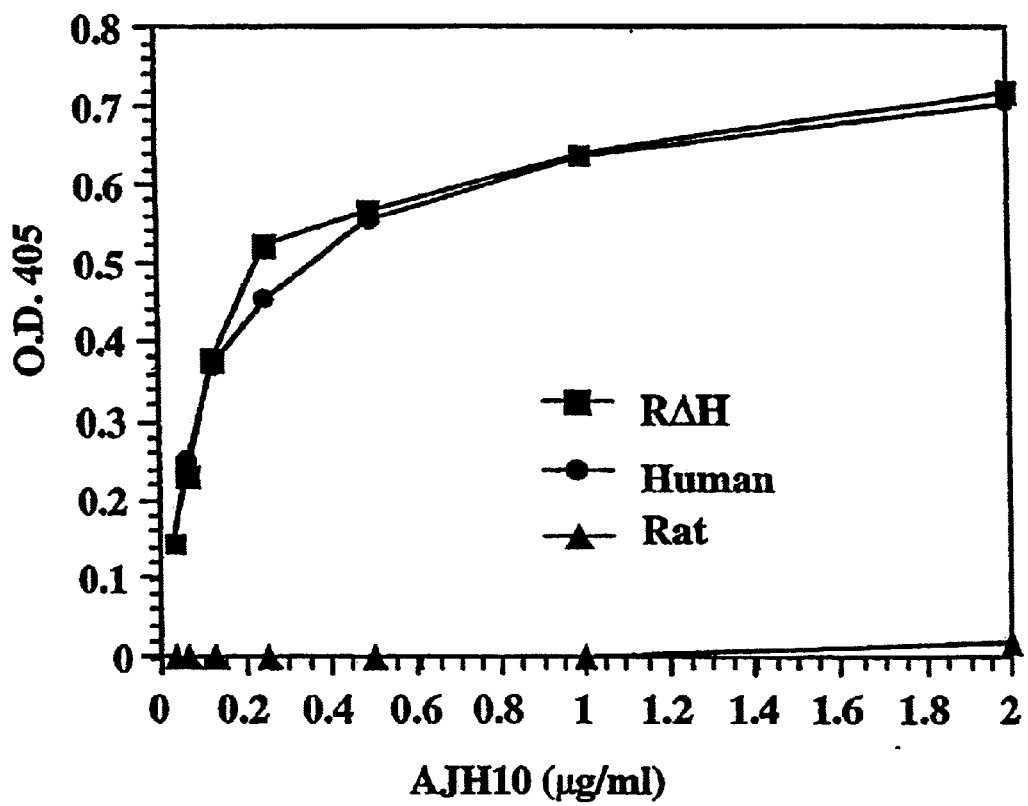
FIG. 4A–FIG. 4B. Location of the Epitope for the anti-α1-I domain Blocking mAbs.

The output of the spectrophotometric data discussed above is determined primarily by the fluorescence of a single buried tryptophan, which lies within the MIDAS region of the α1-I domain (W36, FIG. 4A). Thus, the spectrophotometric data only provide a view of the MIDAS region and not of the entire I-domain.

Example 9

Circular dichroism. To distinguish between local and possible wide range effects on structure, we determined, by measuring circular dichroism spectra in the presence or absence of $Mn^{2+}$ and $Mg^{2+}$, the temperature at which the I domain denatured, and the effect of denaturation on secondary structure of the protein. The circular dichroism measurements described below revealed that cation binding effects not just the local expression of the epitope, but stabilizes the secondary structure of the α1-I domain.

Circular dichroism spectra were recorded using a J-710 spectropolarimeter (JASCO, Japan) equipped with a programmable temperature water bath (CTC-345, JASCO). Far-UV (185–250 nm) and temperature-dependent measurements were performed using U-type cells of path-length 0.0148 cm and volume 0.045 ml with α1-I domain in 20 mM HEPES, 1 mM EDTA, 1 mM DTT, pH 7.5 in the absence of divalent cations, or the presence of either 2 mM $Mg^{2+}$ or $Mn^{2+}$ at a protein concentration of 55 μM. CD spectra were recorded using a scan speed of 20 nm/min, a response time of 2 s and a band-width of 2 nm. Temperature-dependent measurements were performed in the range 10–80° C. The continuous temperature scan at fixed wavelength (222 nm) in the far-UV range was done using a scan rate of 50° C./hr and a response time of 8 s. Data are presented as molar ellipticity per residue.

Figure 8A:
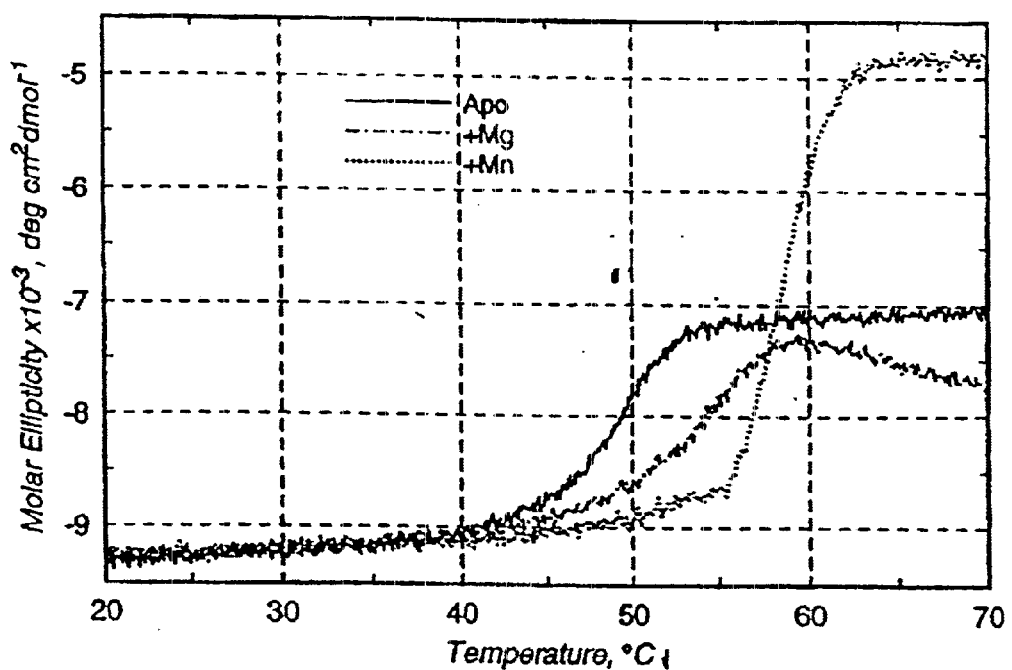
FIG. 8A–FIG. 8B. Circular dichroism spectra of thermally denatured α1-I domain. Temperature dependent, circular dichroism measurements at fixed wavelength (222 nM) were performed using 55 μM α1-I domain in the absence (solid line), or presence of 2 mM $Mg^{2+}$ (dot-dash line), or 2 mM $Mn^{2+}$ (dotted line). Data are expressed as (FIG. 8A) continuous temperature dependence of molar ellipticity per residue, and (FIG. 8B) first derivative curves after smoothing the corresponding data curves shown in panel A.
Figure 8B:
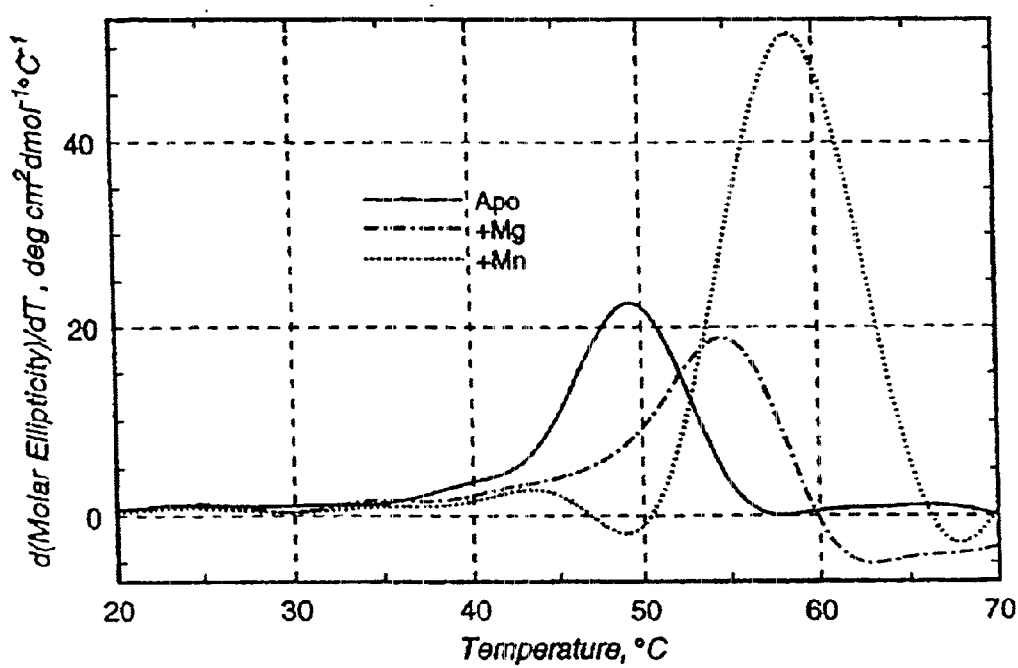

Near and far UV CD spectra for the α1-I domain, in the presence and absence of cation at room temperature, were indistinguishable (data not shown). In contrast, large, cation-dependent differences were seen in the susceptibility of the I domain to thermal denaturation. In the absence of divalent cations, the I domain denatured at $T_m=49.5°$ C. Both $Mn^{2+}$ ($T_m=58.6°$ C.) and $Mg^{2+}$ ($T_m=54.6°$ C.) stabilized the I domain as indicated by increases in $T_m$ (FIG. 8). Heat denaturation in the apo state was accompanied by a 20–25% decrease in ordered secondary structure at 65° C. Decreases of 45% were observed for the $Mn^{2+}$ state at 70° C. and of 34% for the $Mg^{2+}$ state at 80° C. For the apo state, CD spectrum at 65° C. and 80° C. have minima, which are characteristic of a high content of a helical structure whereas in the presence of divalent cations, CD spectra at 70–80° C. have shape that are characteristic for "aggregational" β-structure. These data suggest that, in addition to the local stabilizing effect cations have on the MIDAS region, the presence of cations has a wide ranging effect on the secondary structure of the α1-I domain. It is interesting to note the $Mn^{2+}$ is more stabilizing than $Mg^{2+}$ as evidenced by a greated shift in $T_m$. Since $Mn^{2+}$ is more effective at promoting ligand binding to the α1β1 integrin (Bridges et al. (1995) Mol. Immunol. 32, 1329–1338), the stabilizing effects of $Mn^{2+}$ may be related to the increased affinity of the I domain for ligand.

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention, which is delineated by the appended claims.

What is claimed is:

1. A method for treating lung fibrosis in a subject, the method comprising administering to the subject a pharmaceutical composition comprising an effective amount of an antibody molecule comprising antigen binding regions derived from the light and heavy chain variable regions of an antibody to an α1β1 or α2β1 integrin.

2. The method of claim 1, wherein the antibody molecule comprises antigen binding regions derived from the light and heavy chain variable regions of an antibody to an α1β1 integrin.

3. The method of claim 1, wherein the antibody molecule comprises antigen binding regions derived from the light and heavy chain variable regions of an antibody to an α2β1 integrin.

4. The method of claim 1, wherein the antibody is AJH10 secreted by a hybridoma designated as ATCC PTA-3580.

5. The method of claim 1, wherein the antibody molecule is a human antibody, a chimeric antibody, or a humanized antibody.

6. The method of claim 1, wherein the antibody is a monoclonal antibody.

7. The method of claim 1, wherein the composition is administered parenterally to the subject.

8. The method of claim 1, wherein the pharmaceutical composition further comprises a pharmaceutically acceptable carrier.

* * * * *

SEQUENCE LISTING

```
<160> NUMBER OF SEQ ID NOS: 10

<210> SEQ ID NO 1
<211> LENGTH: 26
<212> TYPE: DNA
<213> ORGANISM: Homo sapien

<400> SEQUENCE: 1
caggatccgt cagccccaca tttcaa                                            26

<210> SEQ ID NO 2
<211> LENGTH: 26
<212> TYPE: DNA
<213> ORGANISM: Homo sapien

<400> SEQUENCE: 2
tcctcgaggg cttgcagggc aaatat                                            26

<210> SEQ ID NO 3
<211> LENGTH: 26
<212> TYPE: DNA
<213> ORGANISM: Homo sapien

<400> SEQUENCE: 3
caggatccgt cagtcctaca tttcaa                                            26

<210> SEQ ID NO 4
<211> LENGTH: 26
```

-continued

```
<212> TYPE: DNA
<213> ORGANISM: Homo sapien

<400> SEQUENCE: 4
tcctcgagcg cttccaaagc gaatat                                              26

<210> SEQ ID NO 5
<211> LENGTH: 214
<212> TYPE: PRT
<213> ORGANISM: Rat

<400> SEQUENCE: 5
```

Val Ser Pro Thr Phe Gln Val Val Asn Ser Phe Ala Pro Val Gln Glu
 1               5                  10                  15

Cys Ser Thr Gln Leu Asp Ile Val Ile Val Leu Asp Gly Ser Asn Ser
            20                  25                  30

Ile Tyr Pro Trp Glu Ser Val Ile Ala Phe Leu Asn Asp Leu Leu Lys
        35                  40                  45

Arg Met Asp Ile Gly Pro Lys Gln Thr Gln Val Gly Ile Val Gln Tyr
    50                  55                  60

Gly Glu Asn Val Thr His Glu Phe Asn Leu Asn Lys Tyr Ser Ser Thr
65                  70                  75                  80

Glu Glu Val Leu Val Ala Ala Lys Lys Ile Gly Arg Gln Gly Gly Leu
                85                  90                  95

Gln Thr Met Thr Ala Leu Gly Ile Asp Thr Ala Arg Lys Glu Ala Phe
            100                 105                 110

Thr Glu Ala Arg Gly Ala Arg Arg Gly Val Lys Lys Val Met Val Ile
        115                 120                 125

Val Thr Asp Gly Glu Ser His Asp Asn Tyr Arg Leu Lys Gln Val Ile
    130                 135                 140

Gln Asp Cys Glu Asp Glu Asn Ile Gln Arg Phe Ser Ile Ala Ile Leu
145                 150                 155                 160

Gly His Tyr Asn Arg Gly Asn Leu Ser Thr Glu Lys Phe Val Glu Glu
                165                 170                 175

Ile Lys Ser Ile Ala Ser Glu Pro Thr Glu Lys His Phe Phe Asn Val
            180                 185                 190

Ser Asp Glu Leu Ala Leu Val Thr Ile Val Lys Ala Leu Gly Glu Arg
        195                 200                 205

Ile Phe Ala Leu Glu Ala
    210

```
<210> SEQ ID NO 6
<211> LENGTH: 214
<212> TYPE: PRT
<213> ORGANISM: Homo sapien

<400> SEQUENCE: 6
```

Val Ser Pro Thr Phe Gln Val Val Asn Ser Ile Ala Pro Val Gln Glu
 1               5                  10                  15

Cys Ser Thr Gln Leu Asp Ile Val Ile Val Leu Asp Gly Ser Asn Ser
            20                  25                  30

Ile Tyr Pro Trp Asp Ser Val Thr Ala Phe Leu Asn Asp Leu Leu Lys
        35                  40                  45

Arg Met Asp Ile Gly Pro Lys Gln Thr Gln Val Gly Ile Val Gln Tyr
    50                  55                  60

Gly Glu Asn Val Thr His Glu Phe Asn Leu Asn Lys Tyr Ser Ser Thr
65                  70                  75                  80

```
Glu Glu Val Leu Val Ala Ala Lys Lys Ile Val Gln Arg Gly Gly Arg
                85                  90                  95

Gln Thr Met Thr Ala Leu Gly Thr Asp Thr Ala Arg Lys Glu Ala Phe
            100                 105                 110

Thr Glu Ala Arg Gly Ala Arg Arg Gly Val Lys Lys Val Met Val Ile
            115                 120                 125

Val Thr Asp Gly Glu Ser His Asp Asn His Arg Leu Lys Lys Val Ile
        130                 135                 140

Gln Asp Cys Glu Asp Glu Asn Ile Gln Arg Phe Ser Ile Ala Ile Leu
145                 150                 155                 160

Gly Ser Tyr Asn Arg Gly Asn Leu Ser Thr Glu Lys Phe Val Glu Glu
                165                 170                 175

Ile Lys Ser Ile Ala Ser Glu Pro Thr Glu Lys His Phe Phe Asn Val
                180                 185                 190

Ser Asp Glu Leu Ala Leu Val Thr Ile Val Lys Thr Leu Gly Glu Arg
            195                 200                 205

Ile Phe Ala Leu Glu Ala
            210
```

<210> SEQ ID NO 7
<211> LENGTH: 6
<212> TYPE: PRT
<213> ORGANISM: Rat

<400> SEQUENCE: 7

```
Gly Arg Gln Gly Gly Leu
1               5
```

<210> SEQ ID NO 8
<211> LENGTH: 6
<212> TYPE: PRT
<213> ORGANISM: Homo sapien

<400> SEQUENCE: 8

```
Val Gln Arg Gly Gly Arg
1               5
```

<210> SEQ ID NO 9
<211> LENGTH: 214
<212> TYPE: PRT
<213> ORGANISM: Homo sapien

<400> SEQUENCE: 9

```
Val Ser Pro Thr Phe Gln Val Val Asn Ser Ile Ala Pro Val Gln Glu
1               5                   10                  15

Cys Ser Thr Gln Leu Asp Ile Val Ile Val Leu Asp Gly Ser Asn Ser
            20                  25                  30

Ile Tyr Pro Trp Asp Ser Val Thr Ala Phe Leu Asn Asp Leu Leu Lys
            35                  40                  45

Arg Met Asp Ile Gly Pro Lys Gln Thr Gln Val Gly Ile Val Gln Tyr
50                  55                  60

Gly Glu Asn Val Thr His Glu Phe Asn Leu Asn Lys Tyr Ser Ser Thr
65              70                  75                  80

Glu Glu Val Leu Val Ala Ala Lys Lys Ile Val Gln Arg Gly Gly Arg
                85                  90                  95

Gln Thr Met Thr Ala Leu Gly Thr Asp Thr Ala Arg Lys Glu Ala Phe
            100                 105                 110
```

```
Thr Glu Ala Arg Gly Ala Arg Arg Gly Val Lys Lys Val Met Val Ile
        115                 120                 125

Val Thr Asp Gly Glu Ser His Asp Asn His Arg Leu Lys Lys Val Ile
        130                 135                 140

Gln Asp Cys Glu Asp Glu Asn Ile Gln Arg Phe Ser Ile Ala Ile Leu
145                 150                 155                 160

Gly Ser Tyr Asn Arg Gly Asn Leu Ser Thr Glu Lys Phe Val Glu Glu
                165                 170                 175

Ile Lys Ser Ile Ala Ser Glu Pro Thr Glu Lys His Phe Phe Asn Val
                180                 185                 190

Ser Asp Glu Leu Ala Leu Val Thr Ile Val Lys Thr Leu Gly Glu Arg
        195                 200                 205

Ile Phe Ala Leu Glu Ala
        210

<210> SEQ ID NO 10
<211> LENGTH: 7
<212> TYPE: PRT
<213> ORGANISM: homo sapien

<400> SEQUENCE: 10

Val Gln Arg Gly Gly Arg Gln
1               5
```